United States Patent
Salehi et al.

(10) Patent No.: US 9,889,087 B2
(45) Date of Patent: Feb. 13, 2018

(54) INTRANASAL DELIVERY OF β2-ADRENERGIC RECEPTOR AGONISTS FOR IMPROVING COGNITION IN HUMANS WITH DOWN SYNDROME AND COMPOSITIONS THEREFOR

(71) Applicant: The Board of Trustees of the Leland Stanford Junior University, Palo Alto, CA (US)

(72) Inventors: Ahmad Salehi, Palo Alto, CA (US); Brian Medina, Palo Alto, CA (US); Van Dang, Palo Alto, CA (US); Devsmita Das, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 14/721,466

(22) Filed: May 26, 2015

(65) Prior Publication Data

US 2016/0184241 A1    Jun. 30, 2016

Related U.S. Application Data

(60) Provisional application No. 62/132,056, filed on Mar. 12, 2015, provisional application No. 62/010,114, filed on Jun. 10, 2014.

(51) Int. Cl.
*A01N 33/02* (2006.01)
*A61K 31/135* (2006.01)
*A61K 9/00* (2006.01)
*A61K 31/167* (2006.01)

(52) U.S. Cl.
CPC .......... *A61K 9/0043* (2013.01); *A61K 31/167* (2013.01)

(58) Field of Classification Search
USPC ........................................................ 514/653
See application file for complete search history.

(56) References Cited

U.S. PATENT DOCUMENTS

| | | | |
|---|---|---|---|
| 5,179,079 A | 1/1993 | Hansen et al. | |
| 5,760,237 A | 6/1998 | Myers et al. | |
| 6,490,472 B1 | 12/2002 | Li et al. | |
| 7,244,703 B2 | 7/2007 | Gyurik et al. | |
| 7,569,586 B2 | 8/2009 | Mammen et al. | |
| 9,320,724 B2 | 4/2016 | Salehi et al. | |
| 2007/0028753 A1 | 2/2007 | Hsu | |
| 2011/0286932 A1 | 11/2011 | Koronyo et al. | |
| 2012/0125330 A1* | 5/2012 | Briant | A61M 15/0045 128/203.15 |
| 2014/0235726 A1* | 8/2014 | Salehi | A61K 45/06 514/630 |

OTHER PUBLICATIONS

Van Dang et. al. (Biol. Psychiatry (Feb. 1, 2014) 75:179-188).*
Alford, K.A. et al. (Apr. 8, 2010, e-published Feb. 12, 2010). "Perturbed hematopoiesis in the Tc1 mouse model of Down syndrome," *Blood* 115(14):2928-2937.
Berthault, F. et al. (May-Jun. 1997). "A fatal case of betaxolol poisoning," *J Anal Toxicol* 21(3):228-231.
Das, I. et al. (Sep. 2011, e-published Aug. 4, 2011). "The use of mouse models to understand and improve cognitive deficits in Down syndrome," *Dis Model Mech* 4(5):596-606.
Davisson, M.T. et al. (1993). "Segmental trisomy as a muse model for down syndrome," in *The Phenotypic Mapping of Down Syndrome and Other Aneuploid Conditions*, 1993 Wiley-Liss, Inc. pp. 117-133.
Edgin, J.O. et al. (Sep. 1, 2010). "Development and validation of the Arizona Cognitive Test Battery for Down syndrome," *J Neurodev Disord* 2(3):149-164.
Howard, J.H. Jr. et al. (Jan. 2004). "Implicit spatial contextual learning in healthy aging," *Neuropsychology* 18(1):124-134.
Lichter, I. et al. (Jun. 1986). "Differential effects of atenolol and enalapril on memory during treatment for essential hypertension," *Br J Clin Pharmacol* 21(6):641-645.
Olson, L.E. et al. (Jul. 2004). "Down syndrome mouse models Ts65Dn, Ts1Cje, and Ms1Cje/Ts65Dn exhibit variable severity of cerebellar phenotypes," *Dev Dyn* 230(3):581-589.
Ramos, B.P. et al. (Mar. 2007, e-published Dec. 28, 2006). "Adrenergic pharmacology and cognition: focus on the prefrontal cortex," *Pharmacol Ther* 113(3):523-536.
Ruparelia, A. et al. (Oct. 2012, e-published May 30, 2012). "Cognitive and pharmacological insights from the Ts65Dn mouse model of Down syndrome," *Curr Opin Neurobiol* 22(5):880-886.
Salehi, A.et al. (Nov. 18, 2009). "Restoration of norepinephrine-modulated contextual memory in a mouse model of Down syndrome," *Sci Transl Med* 1(7):7ra17.

* cited by examiner

*Primary Examiner* — Marcos Sznaidman
(74) *Attorney, Agent, or Firm* — Mintz Levin Cohn Ferris Glovsky and Popeo, P.C.

(57) ABSTRACT

A method of improving cognition in a patient with Down syndrome, which entails intranasally administering one or more β2-ADR agonists or pharmaceutically-acceptable salts of either or both to the patient in an amount and with a frequency effective to improve cognition of the patient as measured contextual learning tests.

10 Claims, 13 Drawing Sheets

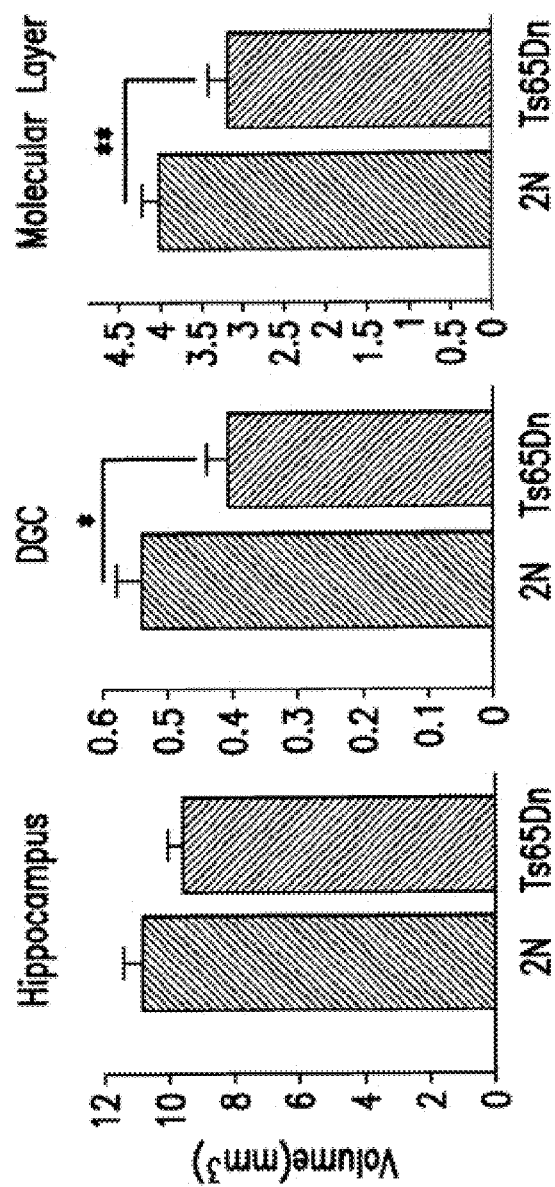
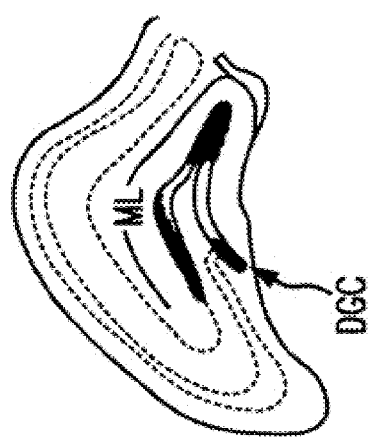

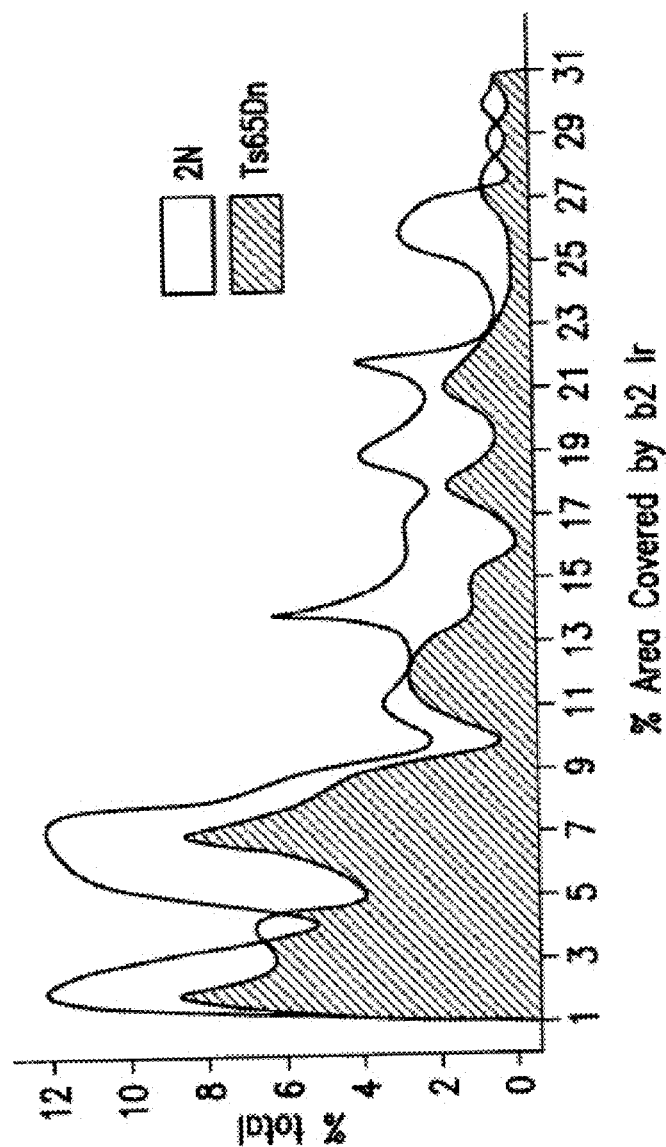
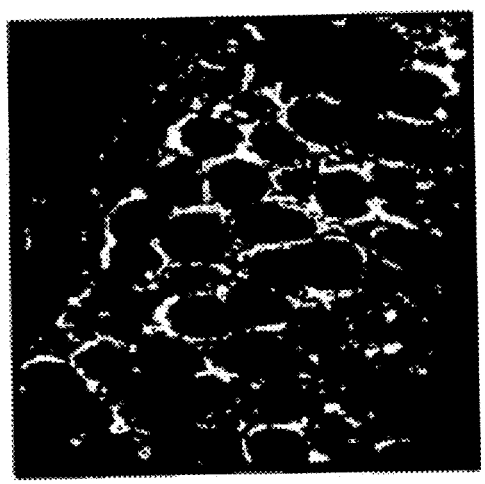
FIG. 3H
FIG. 3G

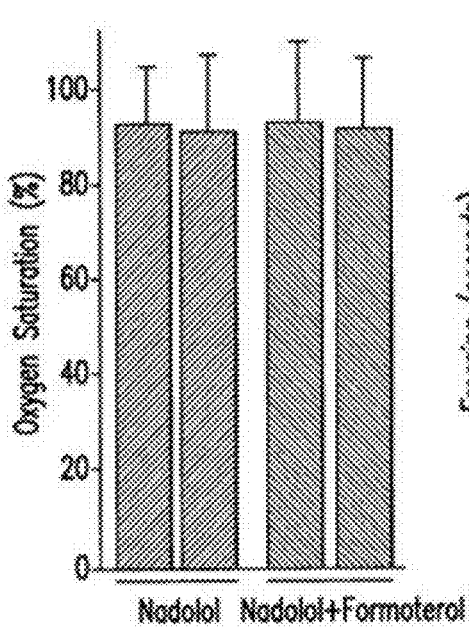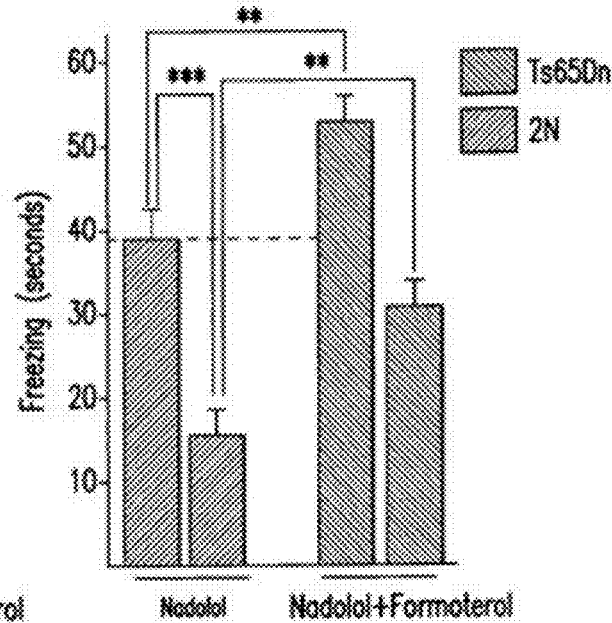
FIG. 4A        FIG. 4B
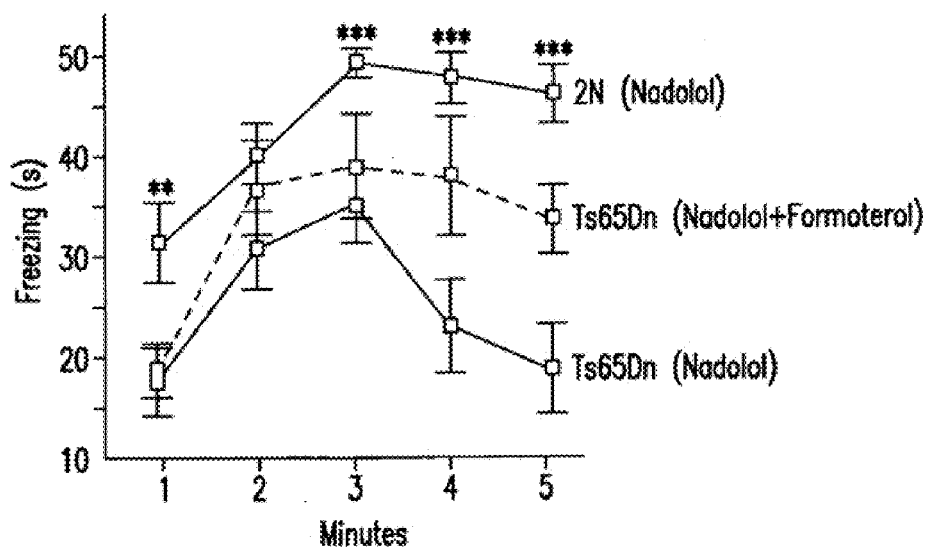
FIG. 4C

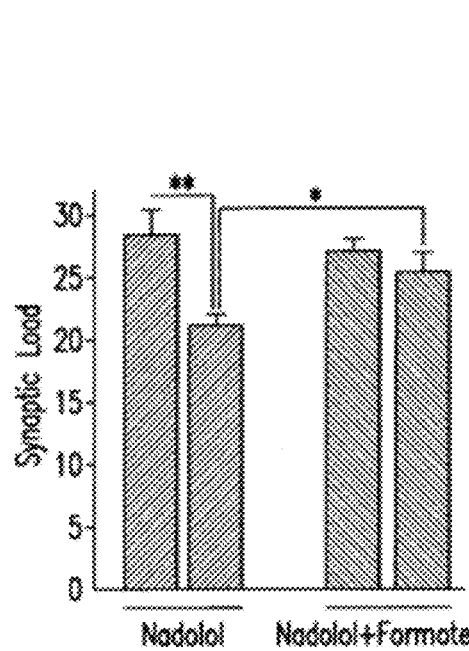
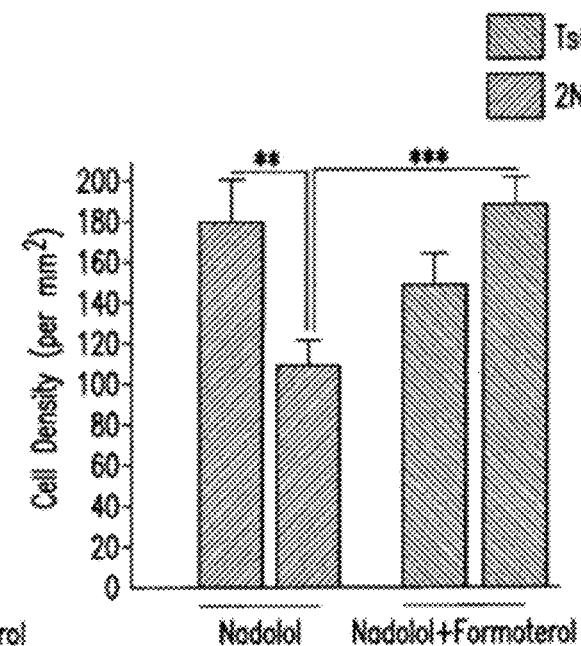
FIG. 6A    FIG. 6B
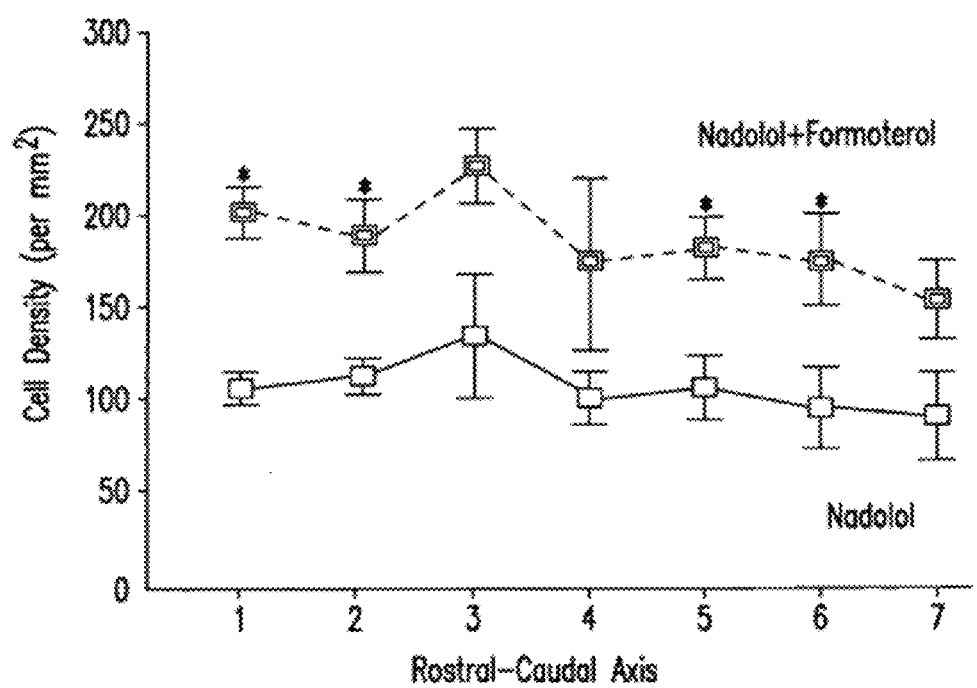
FIG. 6C

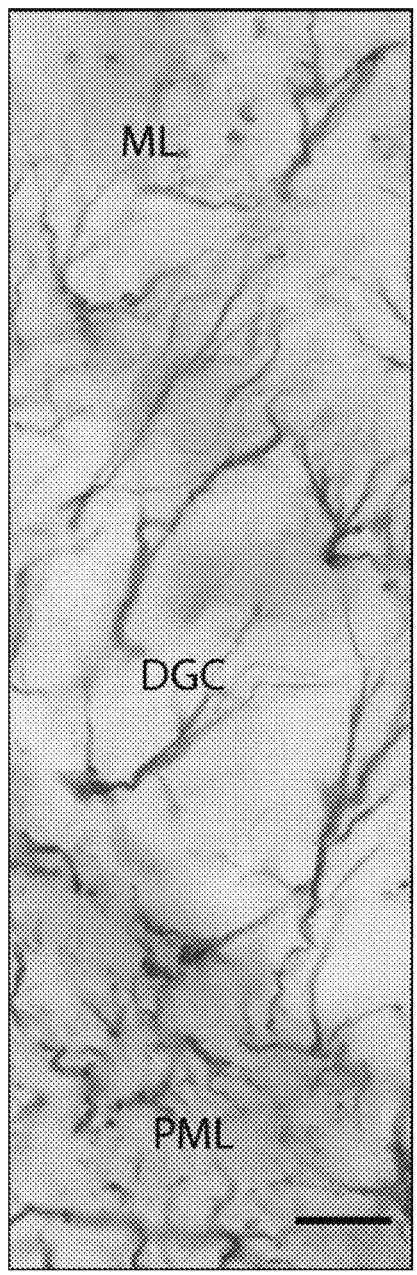
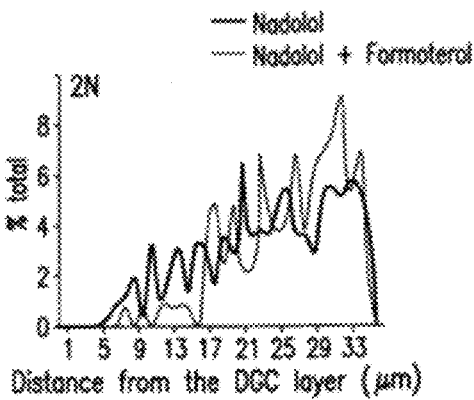
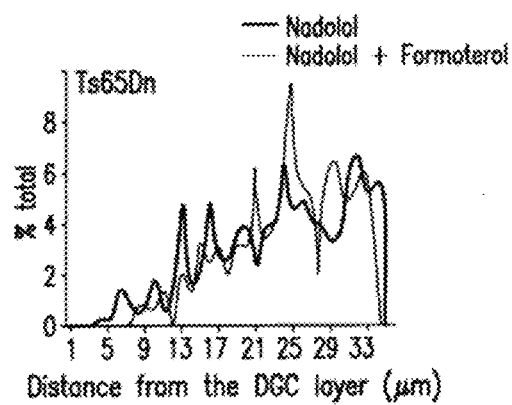
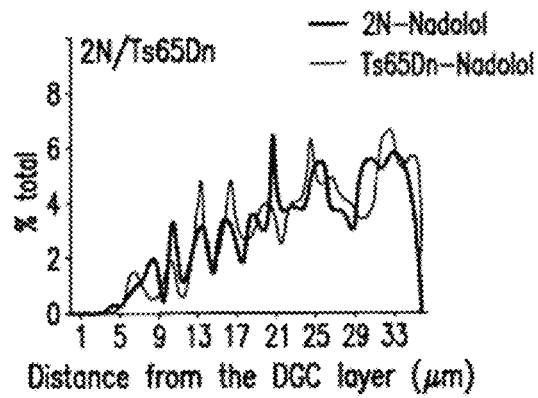
FIG. 7A
FIG. 7B
FIG. 7C
FIG. 7D

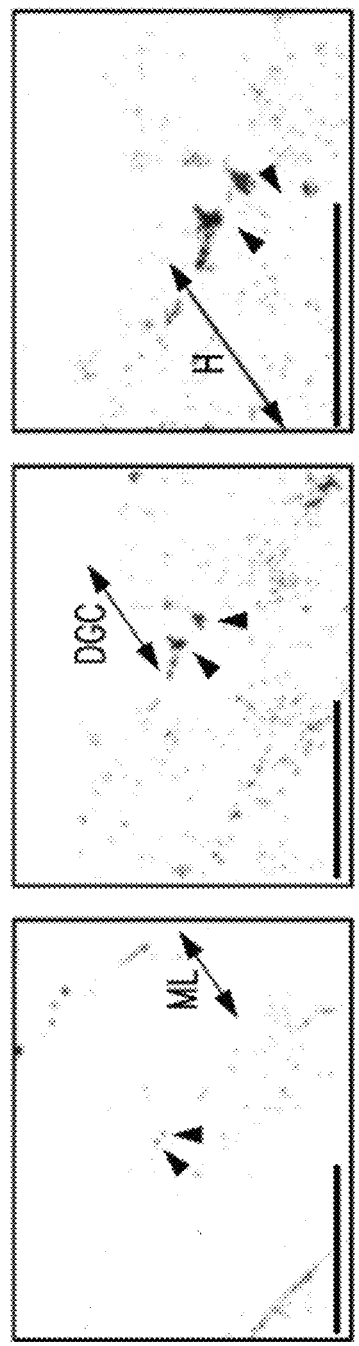
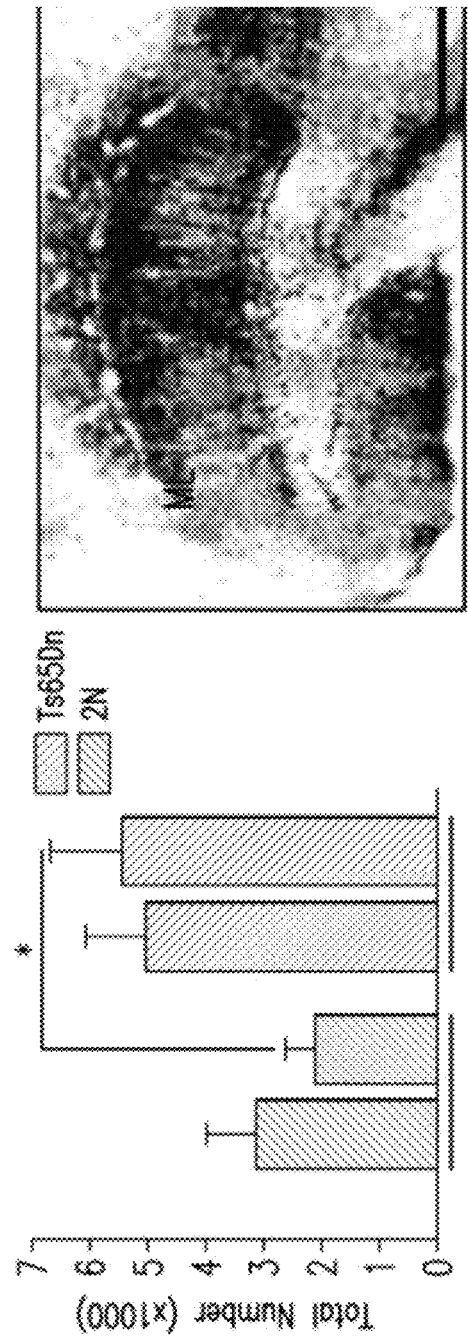
FIG. 8A  FIG. 8B  FIG. 8C  FIG. 8D  FIG. 8E

INTRANASAL DELIVERY OF β2-ADRENERGIC RECEPTOR AGONISTS FOR IMPROVING COGNITION IN HUMANS WITH DOWN SYNDROME AND COMPOSITIONS THEREFOR

CROSS-REFERENCES TO RELATED APPLICATIONS

This applications claims the benefit of U.S. Provisional Application No. 62/010,114, filed Jun. 10, 2014, and U.S. Provisional Application No. 62/132,056, filed Mar. 12, 2015, each of which is incorporated herein by reference in its entirety and for all purposes.

SEQUENCE LISTING

The instant application contains a Sequence Listing which has been submitted electronically in ASCII format and is hereby incorporated by reference in its entirety. Said ASCII copy, created on Feb. 18, 2016, is named 41243-517001US)_SL and is 1,669 bytes in size.

BACKGROUND OF THE INVENTION

Worldwide, there are more than 5.8 million individuals with Down syndrome (DS). It is a complex multi-system, e.g. nervous, cardiovascular and digestive, disorder causing significant physical and psychological abnormalities throughout the lifespan of affected individuals. Nervous system dysfunction is the major cause of disability in individuals with DS. Co-morbidity between cognitive dysfunction and psychiatric conditions particularly, attention deficit hyperactivity disorder, further complicates the clinical symptomatology presented by DS. Later in adulthood, all individuals with DS develop brain pathology indistinguishable from that of Alzheimer's disease (AD). As a result, drastic improvement in the life expectancy of people with DS has been associated with a significant increase in the rate of dementia of AD type in these individuals. For this reason, there is an emerging need for developing effective therapeutic strategies for cognitive disabilities in children before the occurrence of AD pathology in their adulthood. By both increasing cognitive function in children with DS, and delaying of AD brain pathology as these children reach adulthood, humans with DS will be capable of living longer, more productive lives.

SUMMARY OF THE INVENTION

The present invention provides a method of improving cognitive function in humans exhibiting DS using intranasal administration of one or more β2-adrenergic receptor (ADR) agonists or compositions containing the same.

The present invention also provides pharmaceutical compositions for intranasal administration for improving cognition in humans exhibiting DS, the compositions containing one or more β2-ADR agonists.

The present invention further provides a method for inhibiting onset of adult AD brain pathology in people with DS using intranasal administration of one or more β2-ADR agonists or compositions containing the same.

BRIEF DESCRIPTION OF THE DRAWINGS

FIGS. 1A-1D illustrate volume of the hippocampus and different layers of the DG in naive adult Ts65Dn mice and their 2N controls. FIGS. 1B-1D show a significant shrinkage of the DG area in Ts65Dn mice. FIG. 1A depicts a schematic representation of the hippocampal region and the sub-regions of the dentate gyms (DG). FIG. 1B depicts volume results from the hippocampus. FIG. 1C depicts volume results from the dentate granular cells (DGC). FIG. 1D depicts volume results from the molecular layer (ML).

FIG. 2A depicts location of a micro-punch through the DG of the hippocampus that was analyzed here. FIG. 2B is a histogram depicting reduction in cAMP levels in DG area of Ts65Dn mice compared with 2N mice. These figures suggest that there is a significant reduction in NE signaling in the hippocampus of Ts65Dn mice.

FIG. 4A shows the effects of formoterol treatment on oxygen saturation in 2N and Ts65Dn mice. Oxygen saturation was quantified in each mouse using an infrared detector. This figure shows that formoterol together with nadolol had no significant effects on oxygen saturation in both 2N and Ts65Dn mice. FIG. 4B depicts histogram of freezing time (seconds) in 2N and Ts65Dn mice. FIG. 4C depicts time course (minutes) of freezing time (second) in 2N and Ts65Dn mice under indicated conditions.

FIG. 6A illustrates that formoterol treatment restored synaptic density in the DG in Ts65Dn mice. The density of synapses is a strong indicator of cognitive function. This figure shows that a significant reduction occurs in the number of synapse in the Ts65Dn mouse model of DS. FIG. 6B depicts histogram showing that a significant reduction in the density of c-Fos-positive DGCs in Ts65Dn mice compared with 2N mice is observed. FIG. 6C depicts quantifying of the density of c-Fos-positive cells in the DGC region across the rostro-caudal axis of the hippocampus in Ts65Dn mice, which showed that formoterol led to a significant increase in the density of c-Fos positive cells throughout along the rostro-caudal axis the hippocampus in these mice.

FIG. 7A shows immunocytochemical visualization of GFAP in the DG of a 2N mouse (Scale bar: 20μ). FIGS.

7B-7D depict frequency distribution of distances of GFAP-positive profiles from the DGC area. X-axes: distances from the DGC layer (um); Y-axes: % total. Mice: 2N (FIG. 7B); Ts65Dn (FIG. 7C); 2N/Ts65Dn (FIG. 7D).

Figure 8F:
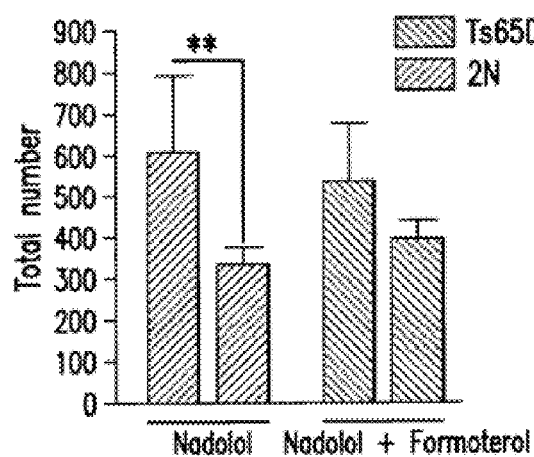
Figure 8G:
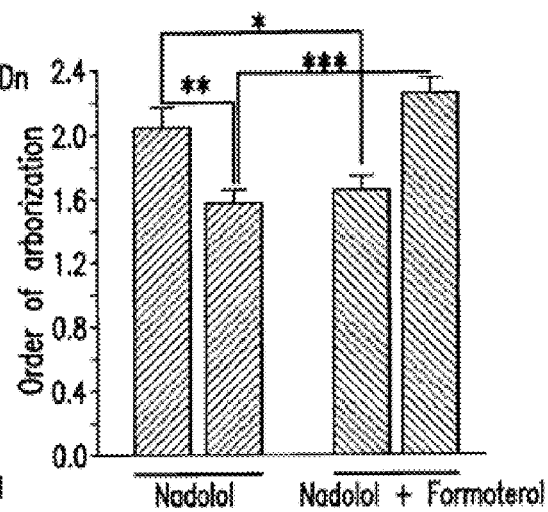
Figure 8H:
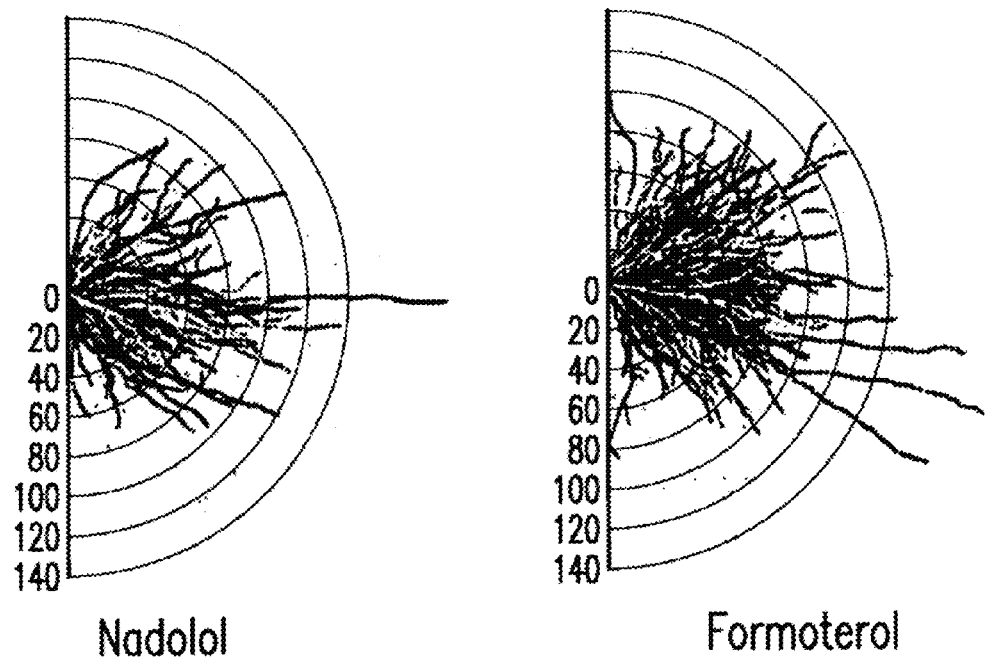

FIGS. 8A-8C illustrate BrdU-positive profiles (arrows) in the DG of a 2N mouse (Scale bar=300μ (FIG. 8A), 100μ (FIG. 8B) and 80μ (FIG. 8C). FIG. 8D depicts histogram showing that the total number of BrdU-positive profiles in the DG was 37% lower in numbers in Ts65Dn mice compared to 2N controls. FIG. 8E is a photomicrograph DCX-positive neurons in the DG of a 2N mouse; Scale bar=170 μm. FIG. 8F is a histogram showing the number of DCX-positive DGCs in 2N and Ts65Dn mice. FIG. 8G is a histogram showing the order of branching in Ts65Dn and 2N mice. FIG. 8H depicts that the increase in the dendritic span in the formoterol-treated Ts65Dn mice has been clearly demonstrated.

Figure 9:
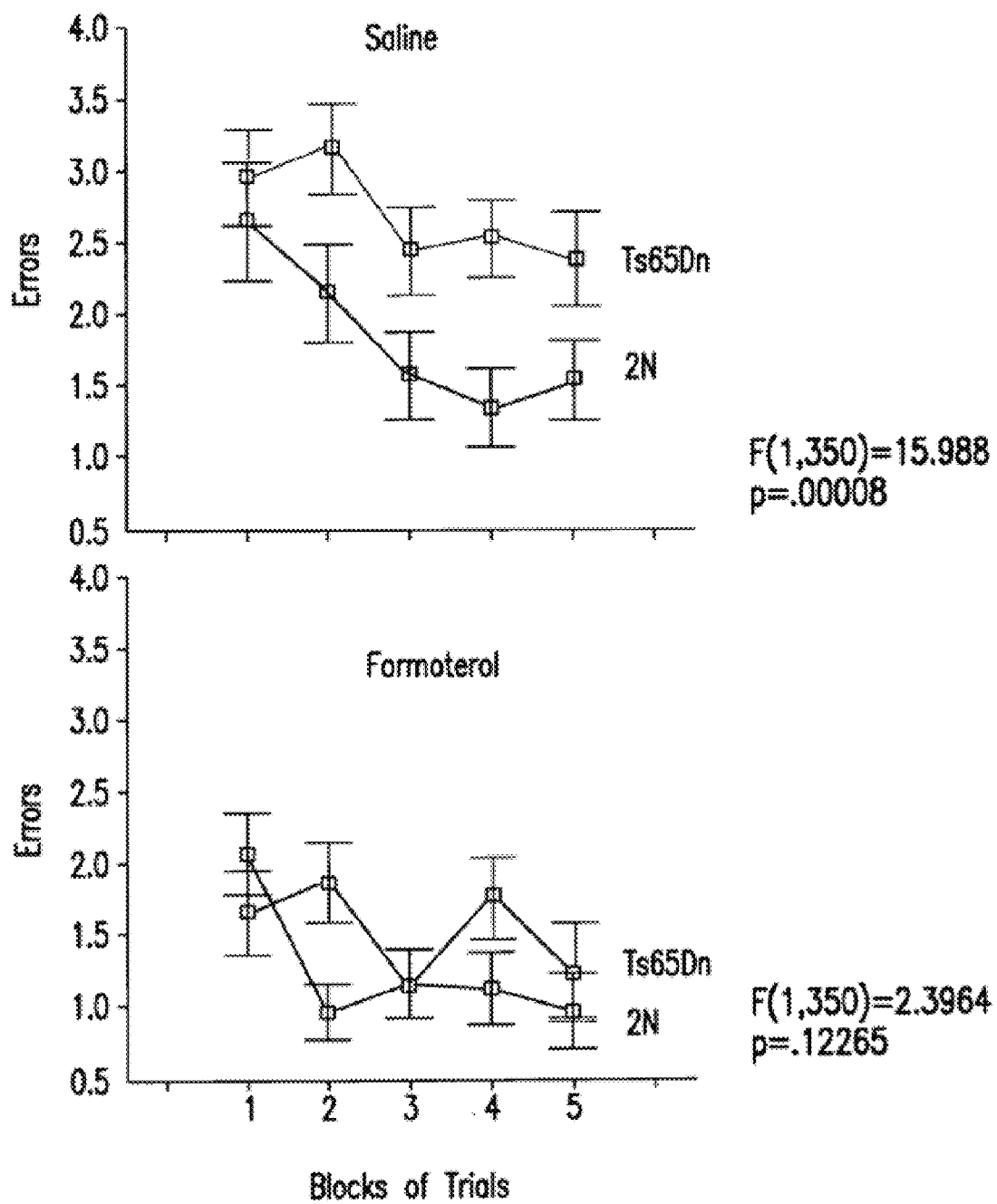

FIG. 9 illustrates the effects of intranasal delivery of formoterol on spatial learning in Ts65Dn mice and their 2N controls. While there was a significant increase in the number of errors and the time to reach the hidden platform in saline-treated Ts65Dn mice compared with their 2N counterparts, no significant differences between formoterol-treated Ts65Dn mice and their 2N controls were found.

Figure 10:
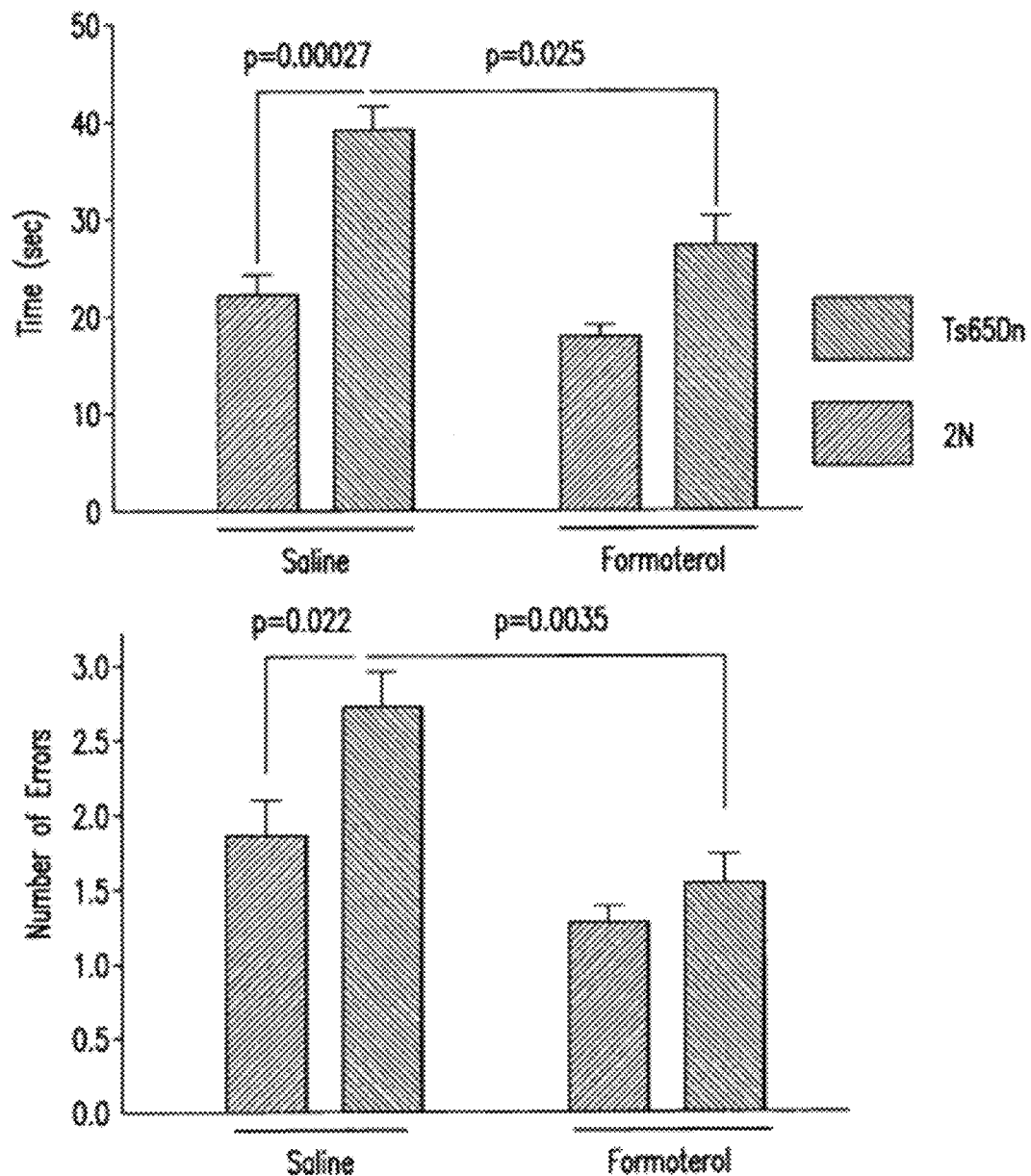

FIG. 10 illustrates average values of the total time and the number of errors made by Ts65Dn and 2N controls treated with intranasal formoterol. Significant effects of formoterol were found in both the time and number of errors in Ts65Dn mice indicating that formoterol led to a significant improvement in spatial learning in these mice.

DETAILED DESCRIPTION OF THE PREFERRED EMBODIMENTS

The present invention is based, in part, upon the discovery that β2-ADR agonists are advantageously used to improve cognition in humans having DS when administered intranasally.

The present invention is also based, in part, upon the discovery that β2-ADR agonists are advantageously used to increase dendritic complexity in humans having DS when administered intranasally.

The present invention is also further based, in part, upon the discovery that β2-ADR agonists are particularly advantageously used to improve cognition and increase dendritic complexity in humans when administered intranasally without any prior or co-administration of one or more β2-adrenergic antagonists.

The present invention is, moreover, based, in part, upon the discovery that onset of adult AD brain pathology in humans having DS can be inhibited by administering one or more β1-ADR agonists to a child having DS using intranasal administration, and also without any prior or co-administration of one or more β1-adrenergic agonists.

We have already demonstrated that the use of the long-acting β2-adrenergic receptor agonists, such as formoterol, led to a significant improvement in cognitive function and increased the synaptic density in the DG of the Ts65Dn mouse when injected intra-peritoneally. Since most β2-ADR are located in the respiratory system, we investigated whether intranasal administration of β2-ADR agonist solutions would lead to any positive effects of cognitive function particularly on spatial learning assessed using radial arm water maze. The results shown in FIGS. 9 and 10 indicate a significant improvement in the spatial learning in Ts65Dn mice as indicated by the time and number of errors that they commit prior to reaching a hidden platform in radial arm size as described below in detail. Further, we have also now discovered that intranasal administration of one or more β2-ADR agonists or compositions containing the same to DS humans is as effective in improving cognition as injection modes of administration, yet intranasal administration also has the additional advantage of avoiding undesirable peripheral effects. This is presumably because intranasal administration affords a direct pathway through the brain through the olfactory bulb.

Term Definitions

As used herein, the term β2 agonist is used to mean β2-adrenergic receptor agonist or β2-ADR agonist. Moreover, the term β2 agonist is understood to include compounds that are primarily β2 agonists, but which may also exhibit some peripheral agonism for other adrenergic receptors, such as β1-adrenergic receptors. In this application, the terms "β2-adrenergic receptor agonist", "β2-ADR agonist", "β2AR agonist" and "β2 agonist" may be used interchangeably. The term β2-ADR agonist expressly includes both selective and partial agonists.

β2 agonists that may be used in accordance with the present invention may be short-acting, long-acting or ultra long-acting. Examples of short-acting β2 agonists that may be used are salbutamol, levosalbutamol, terbuline, pirbuterol, procaterol, metaproterenol, bitolterol mesylate, oritodrine, isoprenaline, salmefamol, fenoterol, terbutaline, albuterol, isoetharine, Examples of long-acting β2 agonists that may be used are salmeterol, bambuterol, formoterol and clenbuterol. Examples of ultra long-acting β2 agonists include indacaterol.

The term "pharmaceutically-accepted salts" means acid addition salts that are commonly used in human or veterinary medicine and are deemed safe for use. Examples for the present invention include, but are not limited to, salts obtained from the following acids: acetic, ascorbic, benzenesulfonic, benzoic, camphosulfonic, citric, ethanesulfonic, edisylic, fumaric, gentisic, gluconic, glucoronic, glutamic, hippuric, hydrobromic, isethionic, lactic, nitric, phosphoric, succinic, sulfuric and tartaric, for example. Any hydrated forms of such salts are also included in this definition. Thus, for example, both fumarate and hemifumarate salts are specifically contemplated as well as any hydrates thereof. For example, fumarate dihydrate may be specifically mentioned.

DS means Down syndrome.

AD means Alzheimer's Disease.

AD brain pathology refers to the accumulation of highly degradation-resistant amyloid fibers that cause lesions in areas of the brain proximate thereto. Accumulation of these amyloid fibers to neurotoxic levels leads to destruction of nerve fibers, which, in turn, leads to the observed behavior associated with Alzheimer's dementia. Observed behavioral symptoms, which become progressively more severe with progression of the disease, often include loss of vocabulary, incorrect word substitutions (paraphasias), loss of reading and writing skills, increased risk of falling, wandering, loss of speech, apathy and even loss of muscle mass.

Child, as used herein, means a human from about 5 to 20 years of age.

Adult, as used herein, means a human from about 21 years of age and older.

Test, as used herein, refers to a contextual learning test, and as applied to humans means specifically a spatial contextual learning test or the ACTB, described below.

Improving cognition means an improved score on a contextual learning test or the ACTB test as described hereinbelow.

The term "therapeutically effective amount" means an amount of a compound or composition as described hereinbelow effective or sufficient to improve cognition and/or inhibit onset of adult AD pathology. The term "frequency" as related thereto means the number of times a treatment is administered to a DS human in order to obtain the result of improved cognition and inhibition of adult AD pathology. In this application, the term "therapeutically effective amount refers to intranasal administration.

Intranasal delivery means delivery of a compound or pharmaceutical composition through the nose and preferably through the nose by applying drops, liquid spray, dry powder spray, using nasal swabs or nasal inhaler to the nares. For example, the compounds and compositions may be intranasally administered using any device or formulation as described in U.S. Pat. Nos. 5,179,079 or 7,244,703, or US pub. 2007028753, all of which are incorporated herein in the entirety. Nasal drop formulations are preferred due to the simplicity of administration. The term 'swab' means any device that contains a support that is narrow enough to enter the nares with an absorbent material at the end that may be dipped in an aqueous solution of the β2-ADR agonists. For example, a Q-tip-configured device is exemplary.

Creation of several trisomic mouse models has greatly facilitated progress in the understanding the neurobiological basis of cognitive dysfunction in DS. Among the mouse models, the Ts65Dn mouse is best characterized. It has an extra copy of approximately 140 mouse genes on chromosome 16, orthologous to those on human chromosome 21 (HSA21). Almost all genes in HSA21 with potential role in nervous system abnormalities are also found in Ts65Dn mice. Similar to DS, alterations in the structure and function of the hippocampus and failure in the induction of long-term potentiation (LTP) have been extensively reported in Ts65Dn mice. Ts65Dn mice are the most widely used in DS research, and are considered to be an art-accepted model for investigations regarding DS in humans. Olson, L. E., et al, Dev. Dyn. 2004 July; 230(3):581-9.

DS is characterized by degeneration and dysfunction of multiple neuronal populations in the central nervous system (CNS). Among them, the hippocampal formation, i.e. the primary site for processing contextual learning shows significant abnormalities in DS. As a result, failure in contextual learning is a common finding in people with DS. To uncover the neurobiological basis of failed contextual learning in DS, we have carefully examined the integrity of subcortical regions extensively projecting to the hippocampal formation. Through extensive innervation, these subcortical regions impose strong modulatory influence on hippocampal neurons. Among these subcortical regions, LC is of particular importance. LC neurons in the brainstem are the sole supplier of massive norepinephrine (NE)-ergic terminals for the hippocampus and play a significant role in wakefulness, attention, and navigational memory. In our previous study, we found significant age-related degeneration of NE-ergic neurons of LC in Ts65Dn mice. Interestingly, the loss of LC terminals in Ts65Dn mice leads to further deterioration of cognitive dysfunction in these mice. Similarly, LC neurons undergo extensive age-dependent degeneration in DS. The critical role of NE-ergic system dysfunction in cognitive dysfunction in Ts65Dn has been supported by the fact that increasing brain NE levels with L-threo-3, 4-dihydroxyphenylserine (L-DOPS), i.e. a NE prodrug, restored contextual learning in Ts65Dn mice. Although L-DOPS is in phase III clinical trial for the treatment of primary autonomic failure associated with Parkinson's disease, it is yet to be approved by the FDA and its long-term effects particularly in children have yet to be explored.

To identify an alternative and to expedite the process of drug development in DS, we tested the effects of adrenergic agonists on cognitive function that have already been approved for use in humans. NE binds to a family of G protein-coupled receptors including a (1 and 2) and β (1, 2, and 3) (AR). Through increasing cyclic adenosine monophosphate (cAMP) and activation of protein kinase A (PKA), β-adrenergic receptor (βAR) signaling plays a major role in memory retrieval and consolidation. The principle neuronal population of the dentate gyms (DG), i.e. dentate granular cells (DGC), plays a major role in contextual learning predominantly express β2ARs. Accordingly, it has also been shown that while β2AR agonists can improve long-term memory and learning, blocking these receptors impairs memory consolidation in chicks. Moreover, the inhibition of LTP by amyloid β in the DG of rodent models of AD, has been found to be rescued by β2ARs agonists.

Another reason in favor of the use of β2-ADR agonists in treating DS when administration by injection is used are the reduced peripheral effects thereof. In the periphery, a majority of β1ARs are found in the cardiovascular system. Since cardiac abnormalities are considered the most common cause of death in people with DS, one would need to avoid the long-term use of drugs targeting the cardiovascular system in treating DS by injection administration. However, since the intranasal administration of the present invention is able to deliver one or more β2-ADR agonists through the olfactory bulb directly to the brain, peripheral effects on the cardiovascular system are greatly minimized to the treated DS human. β2-ADRs express in the olfactory bulb.

For almost half a century, β2ARs have been attractive targets for pharmacological interventions in respiratory disorders. Accordingly, numerous long-acting β adrenergic drugs have been developed and widely prescribed in humans. Formoterol (FORADIL™) is a long-acting β2AR agonist that is highly selective for β2ARs. This drug is currently prescribed for relieving respiratory symptoms associated with asthma, exercise-induced bronchospasms, and chronic obstructive pulmonary disease. The lipophilic nature of formoterol allows it to be easily deposited into the cell membrane facilitating its long-term action on adrenergic receptors. The drug has been shown to cross the blood brain barrier (BBB) and reach the brain in rats and dogs. For instance, it has been shown that intraperitoneal (IP) injections of formoterol in rodents led to a significant increase in expression of interleukins particularly IL-10 in the hippocampus.

As we have previously described, for example, the use of formoterol in adult Ts65Dn mice was safe and led to a significant improvement in contextual learning and restoration of synaptic density in the DG Ts65Dn mice. Furthermore, formoterol treatment was linked to a significant increase in the rate of cell proliferation and dendritic complexity of newly born neurons in the DG. This result clearly evidences that the use of β2ARs as described hereinbelow are effective in improving cognition in humans with DS. Formoterol is a β2-ADR agonist.

In order to further illustrate the present invention, reference will now be made to certain examples which are provided solely for purposes of illustration and are not intended to be limitative.

EXAMPLES

Figure 1E:
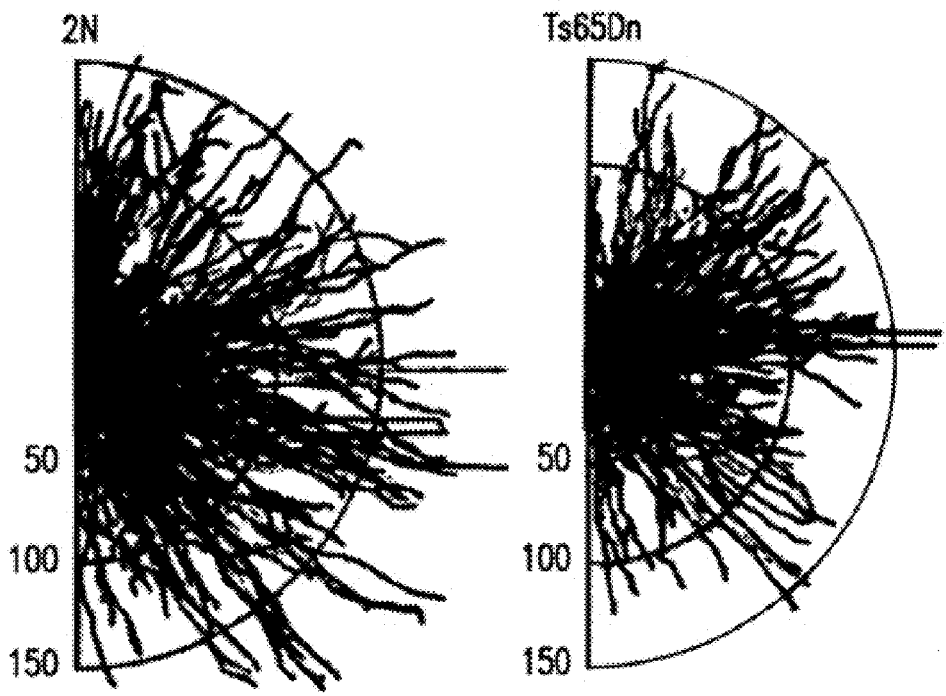
FIG. 1E illustrates the status of dendritic arborization of DGCs in the ML of the DG in naive Ts65Dn mice and 2N mice.
Figure 1F:
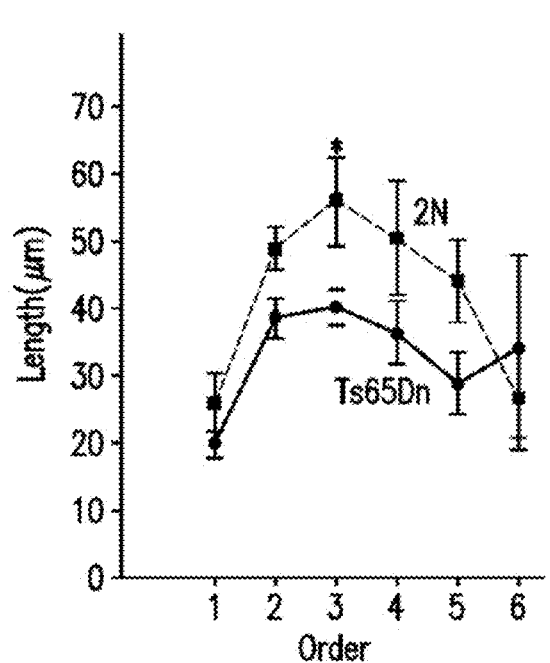
FIG. 1F illustrates a significant reduction in the length of 3rd order dendritic branching of DGCs in Ts65Dn mice.
Figure 1G:
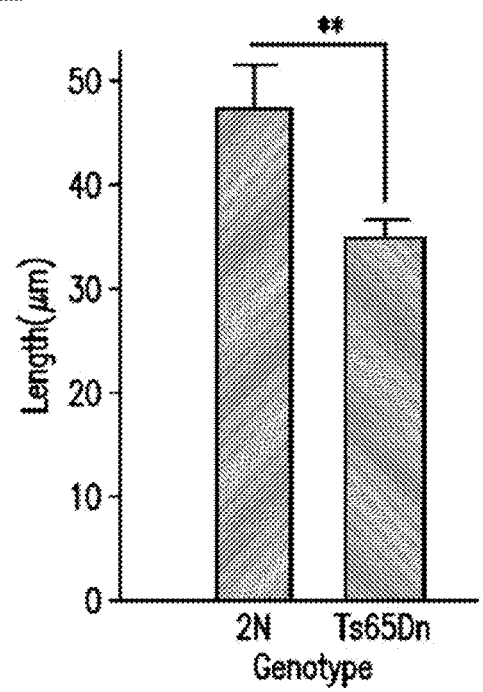
FIG. 1G illustrates a significant reduction in the average length of dendrites in Ts65Dn compared with 2N mice.

The total volume of hippocampus and its sub-regions were quantified in neuronal nuclei (NeuN)-stained brain sections from young adult (6 months) naive mice (FIG. 1A). Although morphometric analyses showed no significant alterations in the hippocampal volume in Ts65Dn mice (FIG. 1B), a significant atrophy of the DGC layer (P=0.032) and the molecular layer (ML) of the DG (P=0.0267) were detected in Ts65Dn mice compared to 2N controls (FIG. 1C, 1D). ML primarily consists of DGC dendrites. To test whether atrophy of DGC and ML in Ts65Dn mice could be linked to alterations in the extent of the dendritic tree, we studied the DGCs' dendrites in adult Ts65Dn mice and their age-matched controls and found a significant shortening of these dendrites in Ts65Dn mice (P=0.016, FIG. 1E, 1F). Interestingly, the analysis of the relationship between dendritic lengths and the order of arborization showed that the most severe shortening of dendrites in Ts65Dn mice occurred in the order 3 (FIG. 1G).

Figure 2A:
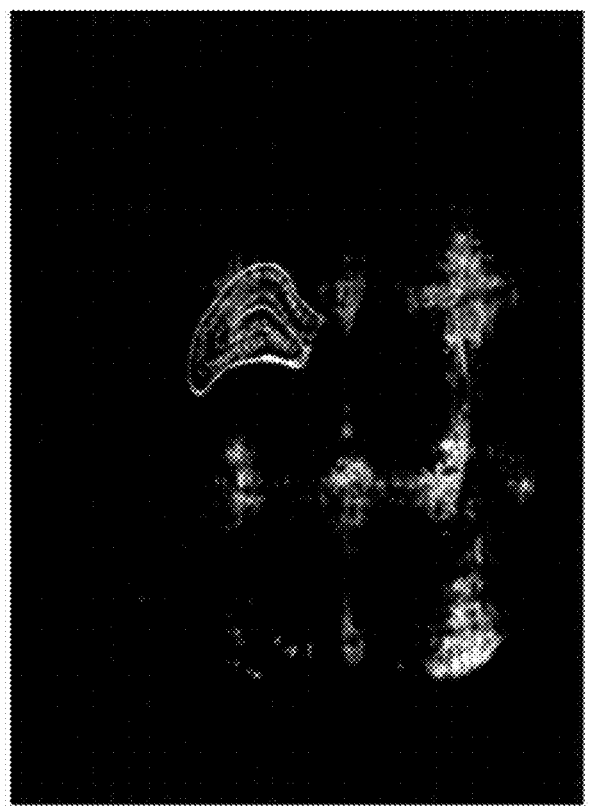
FIGS. 2A-2B illustrate quantification of cyclic adenosine monophosphate (cAMP) levels I (as an indicator of NE signaling) in the DG of naive Ts65Dn and 2N mice.
Figure 2B:
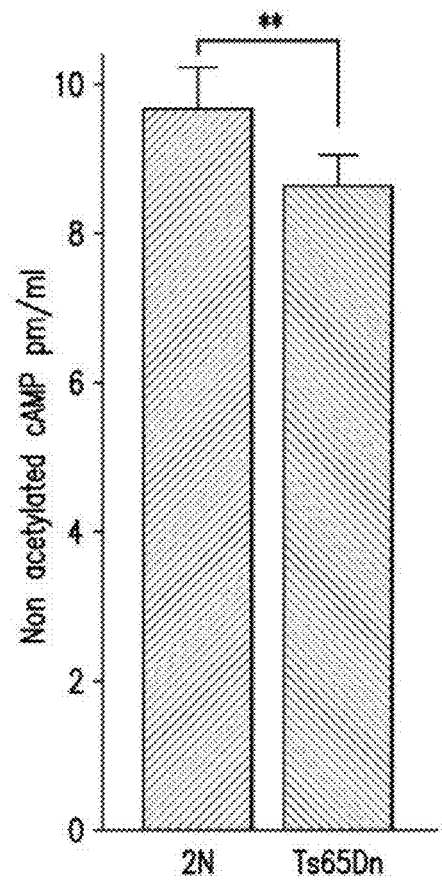

The hippocampal region receives extensive innervation from LC neurons. As we have reported before, LC neurons undergo significant age-dependent degeneration in the Ts65Dn mouse leading to reduced levels of available NE in the hippocampus. Binding NE to ARs leads to the formation of the secondary messenger cAMP, a critical mediator of cell signaling. We asked whether reduced NE levels in the hippocampus in naive Ts65Dn could be linked to alterations in cAMP levels in these mice. Using enzyme linked immunosorbent assay (ELISA), we found significant (P=0.002) reduction in cAMP levels in micro-punches through the DG in adult Ts65Dn mice, suggesting failed AR signaling in the hippocampus in untreated Ts65Dn mice (FIGS. 2A-2B).

Figure 3A:
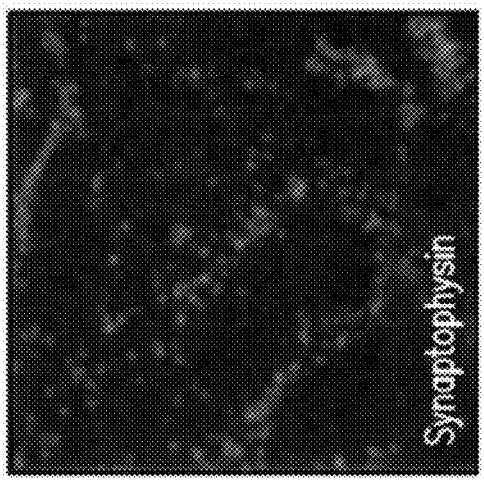
FIGS. 3A-3B depict immunocytological visualization of synaptosphysin (FIG. 3A) and β2AR (FIG. 3B) in DGCs.
Figure 3B:
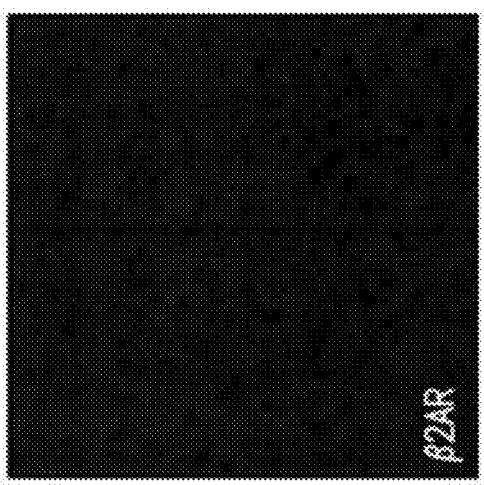
Figure 3C:
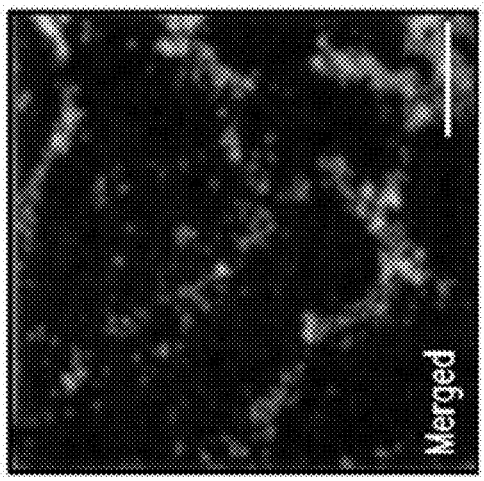
FIG. 3C depicts that the majority of synaptophysin-stained puncta in DGC's soma and cell membrane also contained β2AR immunostaining.
Figure 3D:
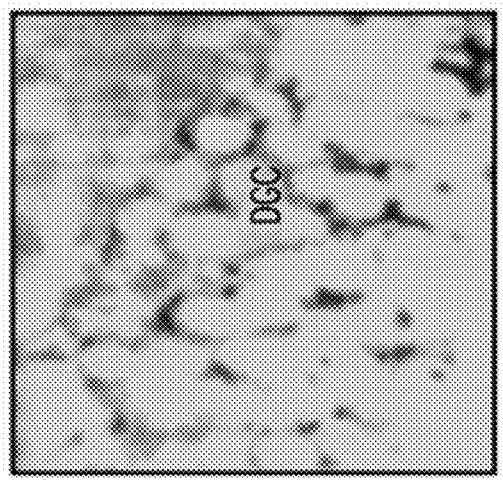
FIG. 3D depicts images taken from GDC cell bodies that were processed for deconvolution (FIG. 3E).
Figure 3E:
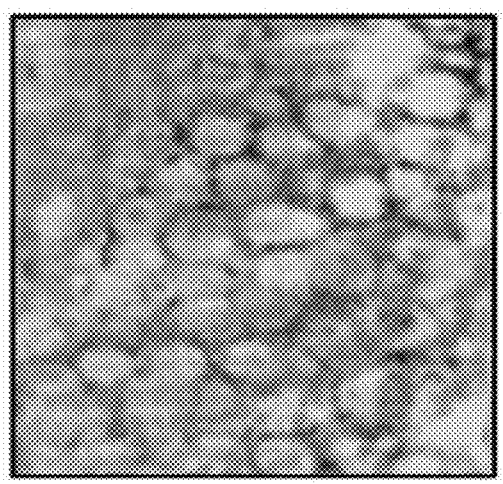
FIG. 3F depicts a mask automatically generated by IMAGE-PRO® Plus was superimposed on each image.
FIG. 3G depicts quantification of the area occupied by the mask.
FIG. 3H depicts quantification of the immunoreactivity for β2ARs. These figures alone show that β2AR receptors are found in pre-synaptic regions in the DG.
Figure 3F:
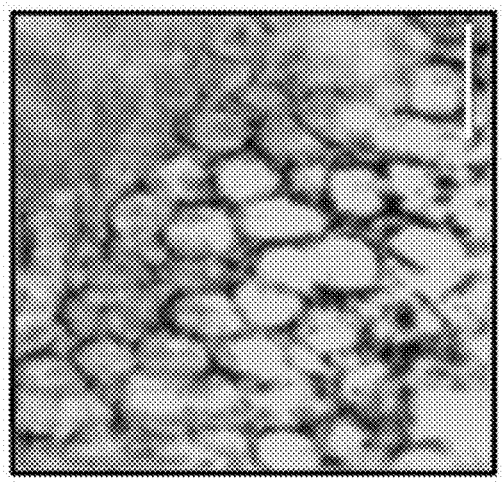

To study the status of β2ARs within the hippocampus, we stained brain sections of adult Ts65Dn mice (5-6 months) and their 2N controls with a polyclonal antibody against β2ARs. Unlike β1ARs that were predominantly found in the polymorphic layer of the DG[12], β2ARs were detected abundantly on the cell membrane of DGCs (FIGS. 3A-3C). Furthermore, a majority of β2ARs were co-localized with a major synaptic vesicle protein, i.e. synaptophysin, in DGCs. Frequency distribution of the area covered by β2ARs staining within the DGC layer (FIGS. 3D-3G) showed a significant (P<0.0001, $X^2$=91.343) shift to the higher values in adult Ts65Dn (FIG. 3H) compared with 2N mice. Furthermore, the analysis of β2ARs in hippocampal synaptosomes showed a trend toward increased levels of β2ARs in the synaptosomes in Ts65Dn mice (2N=102.144±13.85; Ts65Dn=115.680±13.59, P=0.206), suggesting that β2AR remains intact in Ts65Dn mice in spite of significant LC degeneration.

The lack of significant decrease in β2ARs in Ts65Dn mice encouraged us to test the effects of a β2AR agonist, i.e. formoterol on cognitive function in these mice. Since β2ARs are mainly found on the smooth muscle cells in the respiratory system, we started by investigating the effects of formoterol on the respiratory as well as cardiovascular systems. To counter the peripheral effects of formoterol when injected, we used nadolol, i.e. a β1-ADR antagonist that does not cross the BBB. Analysis of variance (ANOVA) showed no significant effects of either genotype or treatment on oxygen saturation (FIG. 4A, genotype: P=0.120, F=2.595; treatment: P=0.259, F=1.335) or the heart rate (genotype: P=0.104, F=2.852; treatment: P=0.369, F=0.839). However, we found a significantly higher respiratory rate in Ts65Dn compared with 2N controls (genotype: P=0.002, F=11.82; treatment: P=0.770, F=0.09). Accordingly, Fisher's post-hoc analysis showed significantly higher respiratory rate (11%) in Ts65Dn compared with 2N mice (P=0.028).

The lack of observed peripheral effects with formoterol treatment in Ts65Dn and 2N mice encouraged us to proceed with testing the effects of formoterol treatment on cognition in Ts65Dn mice. Similar to our previous study, we found significant failure in contextual learning in young adult (6 months) Ts65Dn mice (FIGS. 4B, 4C). Interestingly, treating Ts65Dn mice with formoterol led to a significant improvement in their contextual learning (P<0.0001, FIG. 4B). Quantifying the rate of freezing within the first five minutes of exposure to the context in which they were initially shocked, Ts65Dn mice treated with formoterol showed a significant increase in freezing behavior compared with the Ts65Dn mice treated with only nadolol (P<0.0001, FIG. 4C).

Open field activity has been shown to be a reliable tool for assessing cognitive function in Ts65Dn mice. Ts65Dn mice showed significantly higher velocity and total distance travelled as compared to 2N in the open field arena (FIGS. 5A-5D). Interestingly, treatment with formoterol led to a significant reduction in both velocity (P=0.0014, FIG. 5A) and total distance travelled (P=0.001, FIG. 5B) in Ts65Dn mice, suggesting an improvement in their memory and attention.

To further analyze alterations in the pattern of activity, the location of each mouse in the open field arena was automatically determined. The total number of entries (bouts) from peripheral 50% area of the arena to the central 50% area and vice versa was quantified. We found significantly higher number of bouts in Ts65Dn mice as compared to their 2N controls (P=0.002 for central area; P=0.007 for peripheral area). Interestingly, the use of formoterol led to a significant reduction in the number of bouts in Ts65Dn mice (P=0.011 for central area; P=0.017 for peripheral area).

To test whether improving β2-ADR signaling by formoterol would alter hippocampal synaptic strength; we studied presynaptic vesicles in this region. Using an antibody against synaptophysin, we found a significant reduction in the synaptic density in the DG of the hippocampus in Ts65Dn compared with 2N mice (P=0.008). Interestingly, treatment with formoterol led to a significant increase in synaptophysin immunoreactivity in the DG of Ts65Dn mice (P=0.035, FIG. 6A).

To test whether increased β2-ADR signaling would also improve neuronal activity in DGCs, we studied the expression of c-Fos in these cells. Using an antibody against c-Fos, the numerical density of c-Fos positive-cells in the DGC layer was studied. While we found a significant reduction in the number of c-Fos-positive profiles in Ts65Dn mice compared with 2N mice (P=0.0072), treatment with formoterol restored the number of c-Fos positive cells in Ts65Dn mice to that of controls (2N) (P=0.00014, FIGS. 6B, 6C).

In addition to neurons, astrocytes express both β1AR and β2ARs. Indeed, βAR signaling promotes cAMP production in astrocytes. We questioned whether improving β2-ADR signaling would also influence the status of astrocytes in the hippocampus. Using an antibody against glial fibrillary acidic protein (GFAP), sections throughout the septo-temporal extent of the hippocampus were stained. A large number of astrocytes were labeled throughout the DG. Indeed, most DGCs in the hippocampus were surrounded by numerous astrocytes (FIG. 7A). Interestingly, while we found a significant increase in the density of GFAP-positive profiles in the DG of Ts65Dn mice (P=0.045), no effects of formoterol treatment were detected on either the density of GFAP-positive cell bodies or their processes. Studying the position of GFAP-positive profiles in relationship to the ML, we found that formoterol treatment was associated with a significant increase in the distance between the GFAP-immunoreactive profiles and the DGC layer in Ts65Dn mice (P=0.032, FIGS. 7B-7D).

We studied whether improving β2 signaling with formoterol could also alter the rate of cell proliferation and neurogenesis in Ts65Dn mice. To achieve this, we used 5-bromo-2-deoxyuridine (BrdU), i.e. a synthetic nucleotide that can be incorporated into the newly synthesized DNA of replicating cells. Both 2N and Ts65Dn mice were treated with either nadolol alone or a combination of nadolol and formoterol, followed by BrdU treatment. We found a significant number of BrdU-positive profiles in the sub-granular region of the DG in both Ts65Dn and 2N mice (FIG. 8A). Stereological counting of the total number of BrdU-positive profiles revealed 37% reduction in the DGC layer in Ts65Dn mice compared to 2N mice (FIG. 8A). Interestingly, the treatment with formoterol led to around 1.5-folds increase in Ts65Dn mice (P=0.031, FIG. 8B) and 0.6 folds increase in 2N mice (P=0.191), in the number of BrdU-positive profiles. ANOVA showed significant effects of treatment (P=0.018, F=6.749) and no effects of genotype (P=0.762, F=0.094) on the number of BrdU-positive profiles in the mice treated with BrdU.

To test whether formoterol treatment would indeed influence neurogenesis, we investigated the effects of formoterol on doublecortin (DCX)-positive DGCs and the extent of their dendrites. We found that a significant number of DGCs and their dendrites were labeled (FIG. 8E). Although we found a significant reduction in the number of DCX-positive neurons in Ts65Dn mice, formoterol treatment had no significant effects on the total number of DCX-positive neurons (FIG. 8F). However, we found that formoterol treatment was associated with a significant increase in the complexity of dendritic tree in DCX-positive neurons in Ts65Dn mice (P=0.000075, FIG. 8G). Interestingly, formoterol treatment also led to a significant decrease in the order of dendritic arborization in 2N mice (P=0.018, FIG. 8H).

In order to identify mechanisms by which β2-ADR signaling promotes cell proliferation, we studied the expression levels of genes believed to induce neurogenesis in the hippocampus. FGF2 has been shown to play a key role in proliferation and differentiation of adult neuronal progenitors. Our real-time PCR experiments showed around 70% reduction in Fgf2 mRNA levels in micro-punches through the DG of Ts65Dn mice compared to 2N counterparts (P=0.015, F=6.099). Although formoterol treatment led to increased gene expression for Fgf2 in both Ts65Dn (20%) and 2N (80%) mice, the increase was only significant in 2N mice (P=0.044, t=−2.084).

DS is characterized by significant degeneration of NE-ergic neurons of LC. These changes have been recapitulated in the Ts65Dn mouse model of DS. LC neurons in the brainstem, project extensively to hippocampal and cortical regions. It has been shown that, in rodents, individual LC neurons can project to both hemispheres or both hippocampal and cerebellar regions within the same hemisphere. Extensive innervation of the hippocampus enables LC neurons to exert a strong modulatory influence on incoming sensory and navigational information to this region. For this reason, it is not surprising that degeneration of LC neurons in DS would lead to significant structural and behavioral abnormalities in the hippocampus of affected individuals.

Although the molecular mechanisms behind the loss of LC neurons in DS have yet to be fully elucidated, studying the role of individual triplicated genes in DS might shed some light on this issue. Among more than 100 triplicated genes in DS, App overexpression has been found to play a major role in LC degeneration in both DS and the Ts65Dn mouse model. Our previous studies have unequivocally linked App overexpression to failed axonal transport in cholinergic neurons in Ts65Dn mice. This suggests that through a similar mechanism; failed axonal transport in LC neurons plays a role in their selective vulnerability in DS.

LC neurons are significantly affected by neurofibrillary degeneration in both DS and AD. Indeed, a recent study found that healthy individuals develop signs of neurofibrillary degeneration in LC neurons as early as 6 years of age. Interestingly, LC degeneration seems to precede the degeneration of other brain regions commonly involved in DS and AD. Our previous investigations revealed significant degeneration of both cholinergic neurons of basal forebrain and NE-ergic neurons of LC in Ts65Dn mice. Since both neuronal populations provide extensive innervation to the hippocampus, we suggested that degeneration of these neurons would lead to "de-afferentation" of the hippocampal region in Ts65Dn mice.

We found significant atrophy of the ML and DGC areas of the DG in adult Ts65Dn mice (FIGS. 1A-1G). Major constituents of the DGC area and the ML are DGCs' cell body and their dendrites respectively. We found a significant atrophy of DGCs and shortening of their dendrites in Ts65Dn mice (FIG. 1B). Interestingly, the most severe shortening occurred in the $4^{th}$ order of branching in DGC dendrites, i.e. an area corresponding to a region of ML with the highest density of β2-ADRs in rodents.

Significant age-depended degeneration of LC neurons, reduced density of NE-ergic terminals, diminished NE levels in the hippocampus, and failed contextual learning in Ts65Dn mice all support failure of NE-ergic system in Ts65Dn mice. In the present study, we also found evidence on failed adrenergic receptors signaling in Ts65Dn mice as suggested by diminished cAMP levels in the hippocampus (FIGS. 2A-2B). Interestingly, increasing brain NE levels using L-DOPS, i.e. a prodrug for NE, could successfully restore cognitive function in Ts65Dn mice in spite of significant LC degeneration. Since L-DOPS is yet to be approved for use in the US, the use of alternative drugs already approved, particularly in children, would be an attractive strategy.

The use of formoterol enabled us to test the effects of improving β2-ADR signaling on cognitive function in mice with significant degeneration of LC neurons. Although formoterol binds to all three human βARs, it shows 300-fold more affinity for β2ARs than β1ARs. This indicates that observed effects of formoterol in this study were predominantly mediated via β2-ADRs. Upregulation of β2-ADRs in the DG in Ts65Dn mice (FIGS. 3A-3H) suggests that, in spite of significant LC degeneration in these mice, β2-ADR signaling is still intact.

Formoterol has been shown to reach the brain within 30 minutes of oral administration in rodents. It has been found that, 3 hours after oral administration of formoterol in rats, the drug concentration in the brain was around 30% of that of plasma. Interestingly, the drug levels in the brain were more stable as compared to that of plasma or lungs. IP injections of formoterol in rodents also led to a significant increase in gene expression for interleukin (IL)-1β and IL-1 receptor-II in cortical and hippocampal samples. Importantly, by using β blockers with and without the ability to cross the BBB, the authors showed that the induction of IL gene expression after formoterol treatment by injection was indeed central.

Figure 5A:
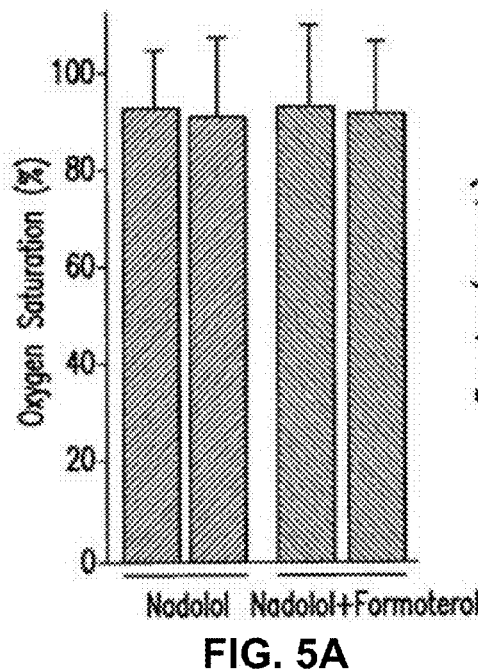
FIG. 5A shows the effects of formoterol on mean velocity in Ts65Dn and 2N mice. This figure shows that open field activity was reduced by formoterol in Ts65Dn mice.
Figure 5B:
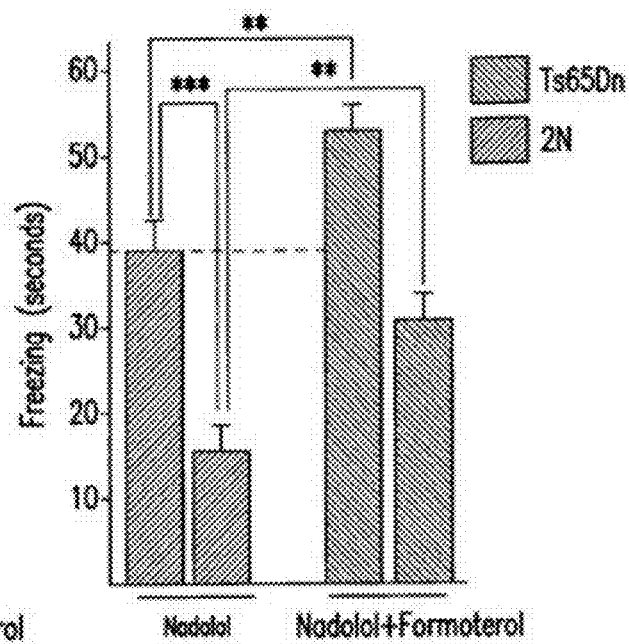
FIG. 5B depicts histogram showing the total distance travelled in 10 minutes under indicated conditions.
Figure 5C:
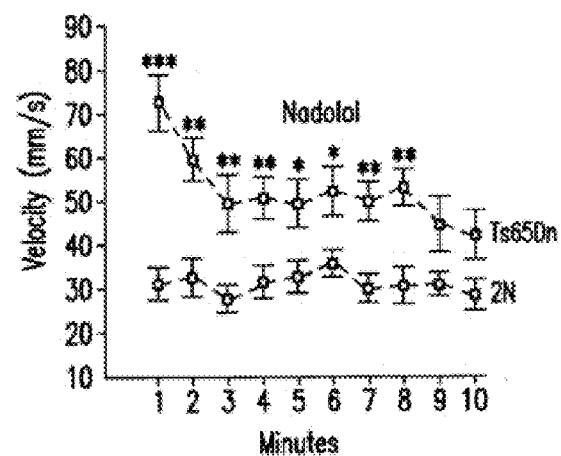
FIG. 5C depicts time course (minutes) of velocity with nadolol treatment in Ts65Dn and 2N mice.
Figure 5D:
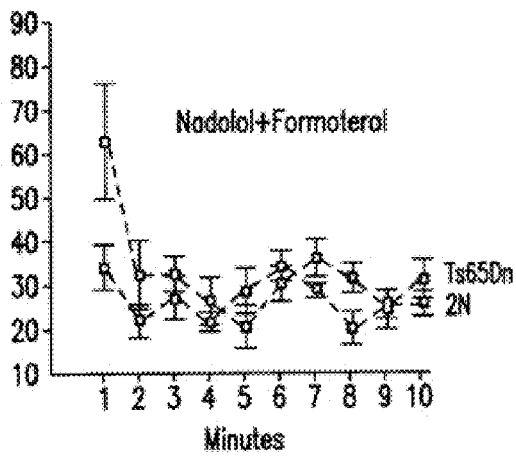
FIG. 5D depicts time course (minutes) of velocity with nadolol+formoterol treatment in Ts65Dn and 2N mice.

We have found that formoterol treatment leads to a significant improvement in contextual learning (FIGS. 4B, 4C) and reduces the severity of hyperactivity (FIGS. 5A-5D) in Ts65Dn mice. In the clinic, formoterol is primarily used for short-term treatment of asthma in humans and leads to significant improvement in respiratory functions. For this reason, we questioned whether the positive cognitive effects of formoterol in Ts65Dn mice were due to its beneficial peripheral effects on the respiratory system. As shown in FIG. 5A, we found no significant effects of formoterol on oxygen saturation in either 2N or Ts65Dn mice (FIG. 4A). This suggests that the observed improvements in cognitive functions in Ts65Dn mice were not due to increased supply of oxygen to the brain.

Our present data indicate that in addition to Ts65Dn mice, treatment with formoterol led to improvement in contextual learning in 2N mice (FIGS. 4B, 4C). The positive effects of adrenergic drugs in 2N mice have been shown before. As we reported before, xamoterol, i.e. a primarily β1AR agonist, can significantly improve contextual learning in Ts65Dn mice. However, later studies suggested that this drug did not improve spatial learning and/or reduce hyperactivity in Ts65Dn mice. The fact that unlike xamoterol, formoterol was able to reduce hyperactivity in Ts65Dn mice (FIGS. 5A-5D) suggests that various aspects of cognition are modulated by different types of β-ADRs. Since formoterol was able to both improve contextual learning and reduce hyperactivity in Ts65Dn mice, this indicates that β2-ADR agonists with the ability to cross the BBB would be attractive therapeutic agents in DS.

Postmortem analysis of the hippocampal samples showed significant deficit in synaptic density in the DG in adult Ts65Dn mice (5-6 months) compared with 2N mice (FIG. 6A). Interestingly, treatment with formoterol led to a significant improvement in Ts65Dn mice restoring synaptic density in DG in these mice. This is in accordance with the observed positive effects of NE and β-ADR agonists on the induction of LTP in the DG in rodents.

c-Fos is an immediate early gene that codes for a 55-kDa nuclear transcription factor, leading to a significant increase in gene expression. It has been shown that treatment with β adrenergic drugs leads to significant increase in c-Fos expression in rodents. To test whether increased β2-ADR signaling led to elevated c-Fos levels in the DG, we studied the levels of c-Fos in DGCs in formoterol-treated animals. While we found a significant reduction in the number of c-Fos-positive profiles in the DGC layer in Ts65Dn mice compared with 2N mice, treatment with formoterol restored the number of c-Fos-positive neurons to normal levels in the Ts65Dn mice (FIGS. 6B, 6C). This suggests that formoterol treatment can lead to a significant increase in neuronal activity and gene expression in DGCs in Ts65Dn mice.

Failure in adult neurogenesis has been suggested to play a significant role in cognitive dysfunction in DS. A significant reduction in cell proliferation has been found in the DG of the dorsal hippocampus in DS fetuses and Ts65Dn mice. Furthermore, both environmental enrichment and a serotonin re-uptake inhibitor i.e. fluoxetine, have shown to promote neurogenesis in Ts65Dn mice. Using BrdU staining, we found 40% reduction in the cell proliferation in the DG in Ts65Dn mice compared with 2N mice. Interestingly, we found that treatment with formoterol led to a significant improvement in cell proliferation in both groups, particularly in Ts65Dn mice (FIGS. 8A-8D). To investigate the fate of the newly born cells in the DG, we used DCX, a microtubule associated protein, as a marker for cells destined to become neurons. While we found a very significant decrease in the number of DCX-positive cells with dendrites in Ts65Dn mice, no effects of formoterol were detected on the total number of DC-positive cells in either genotype. Interestingly, formoterol treatment led to a significant increase in the complexity of dendrites of DCX-positive cells in Ts65Dn mice as shown by the order of dendritic branching (FIGS. 8E-8H). Surprisingly, we also found that formoterol treatment led to a significant reduction in the dendritic complexity in 2N mice (FIGS. 8E-8H). This could suggest that although formoterol treatment can lead to significant improvement in contextual learning in both Ts65Dn and 2N mice, it would induce desirable structural alterations only in the context of abnormal circuits found in Ts65Dn mice.

Ts65Dn mice show a significant increase in the number of astrocytes in DG. β-ADR activation seems to improve the ability of astrocytes to increase $K^+$ clearance during neuronal activity. To test whether formoterol could also alter astrocytes, we studied GFAP-positive profiles in the DG. In accordance to previous studies, we found a significant increase in the number of GFAP-positive profiles in the DG of Ts65Dn mice compared with 2N controls. However, we did not detect any effects of formoterol on the number of astrocytes in either 2N or Ts65Dn mice. Interestingly, we found that formoterol treatment led to a significant increase in the distance between GFAP-positive profiles in the ML and DGC layer in both 2N and Ts65Dn mice.

Taken together, our data suggests that, through improving neurogenesis, increasing dendritic complexity, and thus synaptic strength, β2-ADR agonists significantly improve contextual learning in the Ts65Dn mouse model of DS. This indicates that improving β2-ADR signaling is an attractive strategy in treating cognitive disabilities in humans with DS. It has recently been shown that increasing brain NE levels can also reduce the severity of amyloid pathology in mouse models of AD. Since all adults with DS will eventually develop AD-related pathology, these findings suggest that NE-based therapy can potentially improve cognitive function in children and reduce the severity of amyloid pathology in adults with DS.

Methods

Mice. Adult (5-6 month) male Ts65Dn mice (B6EiC3Sn.BLiA-Ts (17<16>)65Dn/DnJ, stock number: 005252) and gender- and age-matched 2N controls (B6EiC3 Sn.BLiAF1/J, stock number: 003647) were used (Jackson Laboratory). All experiments were approved by the Committee on Animal Research at the Veterans Affairs Palo Alto Health Care System. All animals were group-housed on a 12-hour light/dark cycle and fed ad libitum.

Cardiovascular and Respiratory System Monitoring. Peripheral effects of formoterol were assessed using MOUSEOX® Small Animal Vital Signs Monitor (Starr). The monitor was attached to a collar clip with an LED sensor to enable recordings in free-moving mice. To minimize stress before recording, the collar clip was attached to each animal. After five minutes, heart rate, respiratory rate, and oxygen saturation were recorded using MOUSEOX® 6.3.13 for 10 minutes.

Behavioral Testing a) Open Field Activity. Prior to testing, the mice were handled for five days for habituation. Thereafter, the mice were injected with nadolol and, after one hour, with either saline or formoterol. Four hours later, the mice were tested for open field activity. The open field arena (450 mm×450 mm) had visual cues on the walls. Each mouse was placed in the center of the arena and its movements were recorded for fifteen minutes using a CCD-camera (DM-CO-S20SIE). The arena was cleaned after each session. The velocity, total distance traveled, and the time spent in the peripheral 50% versus central 50% area of the arena (bouts) for each mouse were quantified and analyzed using TopScan Lite (Clever Sys).

b) Fear Conditioning. Since no abnormalities have been found in cued learning in Ts65Dn mice, we only tested contextual learning for this study. The fear conditioning tests were done using four FreezeScan chambers (Clever Sys) on days 4 and 5 after the start of the open field-testing. On day 4 (Training Day), all the mice were injected with nadolol and then, after one hour, with either saline or formoterol. Four hours later, the mice were placed in the fear-conditioning chamber and their baseline activity was recorded for three minutes. At the end of this period, each mouse was exposed to five shocks (2 seconds each, 0.5 mA) with inter-trial intervals of 80 seconds. Twenty-four hours later, the mice were injected again, similar to the Training Day, and returned to the same fear-conditioning chamber for five minutes and their activity was recorded. Freezing was defined as a lack of movement for 3 frames.

Postmortem Analysis. Postmortem analyses were done in two groups of naive and treated mice:

Naive Mice. Adult 2N and Ts65Dn mice were sacrificed using IP injection of sodium pentobarbital (200 mg/kg), trans-cardially perfused with saline, and brain was extracted. The left hemisphere was frozen for gene expression studies, ELISA, and Western blotting. The right hemisphere was fixed in paraformaldehyde overnight at 4° C. followed by dehydration in 30% sucrose and freezing on dry ice. This was followed by embedding each brain in OCT (SAKURA®) and storing in −80°.

a) Synaptosome Preparation.

Hippocampi (n=12 mice per genotype, experiments repeated twice) were collected, pooled (3 hippocampi per sample), and homogenized in homogenization buffer (HB; 0.32 M sucrose, 10 mM Tris, 1× Sigma phosphatase inhibitor cocktail 2 and 3, 1× Roche Complete protease inhibitor tablet). The homogenate was centrifuged and the supernatant was run on successive sucrose gradients, to isolate the enriched synaptosomal fraction (ESF). ESFs were resuspended in lysis buffer (1% Trion, 1% NP40, 0.1% SDS, 0.5% Sodium-deoxycholate, 1× Roche Complete protease inhibitor cocktail, 1× Sigma phosphatase inhibitor cocktail 2 and 3, 2 mM PMSF in DPBS), and lysed, centrifuged, and the supernatant was collected and loaded onto 4-12% Bis-Tris gels (Invitrogen), separated by electrophoresis and transferred to polyvinylidene fluoride membranes. Membranes incubated with a β2AR antibody in TBST overnight, washed and incubated with goat HRP-conjugated antibody (Millipore) in TBST. Immunoreactivity was detected using IMMUNO-STAR™ WESTERNC™ Chemiluminescence Kit (BioRad), and band density was measured using FIJI (NIH).

b) Rapid Golgi Staining. A different group of adult Ts65Dn (5-6 months old) and 2N mice were sacrificed as described above, and their brains were immediately extracted and placed in Rapid Golgi Solution (15 ml per brain, Cornell Center for Technology Enterprise) at RT. Ten days later, the brains were washed, dehydrated and cut (150 µm) using a vibratome (LEICA® CM 1950). All sections were mounted and coated with 50% sucrose. After drying for 72 hours at RT, the sections were rinsed in water and incubated for 10 minutes in the Golgi intensification solution supplied with the kit. The sections were dehydrated and cover-slipped.

c) ELISA Studies. An ELISA kit (Enzo, ADI-900-067) was used for cAMP quantification. The DG region of the hippocampus was punched out using a glass tube under a dissection microscope (Evolution xR6) at −30° C. and stored. The samples were ground to a fine powder under liquid nitrogen and the resulting samples were mixed with 10 volumes of 0.1M HCl followed by centrifugation according to the manufacturer's instructions. The total protein levels were quantified using a micro BCA protein assay kit (23235, Thermo) and spectrophotometer (Fisher) with absorbance at 562 nm.

2) Treated Mice

At the end of behavioral analyses, the mice were injected IP with either nadolol alone or nadolol with formoterol for another 10 days. At the end of this period, all mice were anesthetized, perfused, and the brain was extracted. The right hemisphere from each brain was fixed in 4% paraformaldehyde followed by dehydration. The methodology for staining has been published before. The frozen hemispheres were cut coronally at 70 µm using a cryostat (Leica CM 1950), placed in cryoprotectant solution (25% ethylene glycol, 25% glycerol and 0.05M sodium phosphate buffer), and stored at −20° C. The left hemisphere was flash frozen and used for gene expression studies.

a) Immuno-Staining:

Before all staining(s), to inhibit endogenous peroxidase, 70-µm-thick floating sections were pre-incubated in 0.5% $H_2O_2$ in 50% methanol for 30 minutes at RT. This was followed by pre-incubating the sections in 0.1% triton and 10% normal serums(s) (NS, Vector Labs) for 1 hour at RT. This was followed by incubation in primary antibodies overnight at RT. We used antibodies against synaptophysin (SVP-38, Sigma, S5768), β2AR (SC596, Santa Cruz), GFAP (1:5000; Dako, Z033429), DCX (1:500, sc-8066, Santa Cruz), and c-Fos (1:800; Santa Cruz sc-52). For DCX staining the sections were kept in pre-warmed (37° C.) for 30 minutes before staining. This was followed by incubation in secondary anti-bodies that were diluted in 0.1% triton and corresponding 1% NS. The sections were then incubated in ABC Lite (1:1000, Vector) for 1 hour. Staining was terminated by incubating in DAB (0.66 mg/ml in tris-HCl) for 5-10 minutes. Finally, the sections were washed, dehydrated, and mounted.

b) Synaptophysin-β2AR Co-Localization. Twenty sections were used for this staining. The sections were incubated overnight in a rabbit antibody against β2AR (1:1000). Later, the sections were incubated in a biotinylated anti-rabbit (1:200; Vector) for 1 hour followed by incubation in streptavidin-conjugated Texas Red (Vector) for 1 hour. The sections were incubated with synaptophysin antibody (1:40,000) for 30 minutes. The sections were then incubated with biotinylated anti-mouse (1:650, Jackson ImmunoResearch) for 30 minutes and then with ABC (1:1000) for 1 hour. The synaptophysin staining was visualized using tyramide signal amplification (TSA)-Cy3 (PerkinElmer). Sections were examined a confocal microscopy (Zeiss LSM 510). Excitation was 561 nm laser for both, and emission filters for Cy3 and Texas Red were NFT565 and LP575, respectively.

c) BrdU. To identify proliferating cells, we used 5-bromo-2'-deoxyuridine (BrdU, Sigma). It was dissolved in PBS, filtered, and kept at 4° C. till use. After 15 days of treatment, each mouse was injected IP daily (50 mg/kg) with BrdU solution for 5 days. Thereafter, on day 21, all mice were anesthetized and transcardially perfused with ice-cold saline. The entire brain was immediately removed and the two hemispheres were separated. The left hemisphere was fixed overnight, cut, and stored. Sections were stained using BrdU antibody (1:1000; Millipore, MAB 4072) followed by incubation with biotinylated anti-mouse (1:20,000; Jackson), both for 1 hour. This was followed by incubation of sections in ABC.

Morphometry and Image Analysis

1) BrdU Cell Count. Stereo-Investigator (MBF) was used to quantify the total number of BrdU-positive cells in the entire septo-temporal extent of DG. Following the outlining of the DG area at 4×, each positive profile was identified using a 100× oil objective. Unbiased stereological methods were used to determine the total number of BrdU-immunoreactive-profiles throughout the hippocampus. A Nanozoomer system (Hamamatsu 2.0 RS) was used to capture images of the entire slide in each case. High magnification images were captured using the Nanozoomer and stored.

2) Determination of Dendritic Tree. Golgi-stained 150 μm-thick-sections were used to quantify the extent of dendritic arborization in the ML of DG using Neurolucida. 10-15 DGCs per mouse were traced using 100× oil objective.

3) Image Analysis Methods.

a) Synaptophysin. To examine synaptic load in the DG of the hippocampus, we examined the overall optical density of immunostaining for synaptophysin in a total of 500 images, randomly chosen from the entire polymorphic layer of the hippocampus, and captured at 100× (1280×1200 pixels) using IMAGE-PRO® Plus (MEDIACYBERNETICS®).

b) GFAP Load Quantification. Images throughout the entire septo-temporal axis of the hippocampus were captured using an analogue camera (Cohu) and digitized (10×). The z-axis on each slide was video recorded by moving from top to bottom of each field. The generated video files were decompressed using ImageJ. We performed extended depth of field correction on each video file. As a result, the most focused pixels in each image were transformed to a new composite picture, bringing all GFAP-positive-profiles to the same plane. Based on the optical density of each pixel, a mask was automatically generated. All images were automatically analyzed using IMAGE-PRO® Plus.

c) GFAP-Positive-Profiles Localization Analysis. Separate high-resolution (4076×3116 pixels) images were captured using a 20× objective (Nikon, Eclipse 80i) and stored. The location of each GFAP profile in the ML of the DG was quantified by measuring the distance between each profile and an arbitrary line drawn parallel to the DGC region.

d) β2-ADR Immunoreactivity Quantification. High-resolution images (4076×3116 pixels) were captured using Nikon DS-Ri1 digital camera attached to microscope. Using IMAGE-PRO® Plus, the images were de-convoluted and a mask was made to cover the immunoreactivity of β2 staining in each image (FIG. 4D). The total area covered by the mask was quantified in each image as percentage.

Gene Expression Studies. The left hemisphere of each brain was placed in an aluminum box and snap frozen in liquid nitrogen and stored at −80° C. till use. The brain samples were sectioned coronally at 300 μm thickness. The DG and cerebellum were punched out using a 0.6 mm thick glass tube at −25° C. Total RNA was isolated using TRIZOL®, and treated with DNAse I (Life Technologies). The following primers (IDT) were used:

```
B-actin:
                                     (SEQ ID NO: 1)
    5'-AAATCGTGCGTGACATCAAA-3'  (F);

(SEQ ID NO: 2)
    AAGGAAGGCTGGAAAAGAGC (R),

Gapdh:
                                     (SEQ ID NO: 3)
    TGCACCAACTGCTTAGC (F);

(SEQ ID NO: 4)
    GGCATGGACTGTGGTCATGAG (R),

Fgf2:
                                     (SEQ ID NO: 5)
    5'-CACCAGGCCACTTCAAGGA-3'  (F);

(SEQ ID NO: 6)
    5'-GATGGATGCGCAGGAAGAA-3.
```

Initial cDNA quantity and cycle threshold (CT) for each gene of interest was normalized to the geometrical average of the two normalizers (B-actin and Gapdh). The resulting values were normalized to the values of a 2N mouse, amplified in all plates.

Statistical Analysis. All data are presented in terms of mean±standard error of the mean (s.e.m). The Student t-test was used to compare naive 2N and Ts65Dn mice. We used ANOVA (STATISTICA 6.0, StatSoft) to assess the effects of genotype and treatment on each of the parameters that were quantified. This was followed by a Fisher's least significant difference post-hoc analysis. Differences were considered to be statistically significant when P<0.05.

FIGS. 1A-1G: Volume of the hippocampus and different layers of the DG in naive adult Ts65Dn mice and their controls. (FIG. 1A) Schematic representation of the hippocampal region and the sub-regions of the DG. Unlike the hippocampal volume (FIG. 1B) (2N=11.552±0.70 mm$^3$, n=5, Ts65Dn=10.583±0.51 mm$^3$, n=5, t-value=1.115, P=0.297), we found a significant reduction in the volume of the DGC layer (FIG. 1C) (2N=0.542±0.04 mm$^3$, n=5, Ts65Dn=0.419±0.03 mm$^3$, n=5, t-value=2.574, *P=0.032) and ML (FIG. 1D) (2N=4.057±1.93 mm$^3$, n=5, Ts65Dn=3.256±0.22 mm$^3$, n=5, t-value=2.708, **P=0.026) in Ts65Dn mice compared to 2N mice. (FIG. 1E) The status of dendritic arborization of DGCs in the ML of the DG in naive Ts65Dn mice and 2N mice. Each individual neuron was separately traced and then superimposed at the level of the cell body. Visualization of order of dendritic arborization and quantification of the total length of dendrites in relationship to the order of branching. (FIG. 1F) We found a significant reduction in the length of 3rd order dendritic branching of DGCs in Ts65Dn mice (*P=0.040). (FIG. 1G) A significant reduction in the average length of dendrites in Ts65Dn compared with 2N mice (2N=46.99±4.50 μm, n=5, Ts65Dn=34.65±1.55 μm, n=5, t=−3.01, **P=0.016) was also detected.

FIGS. 2A-2B: Quantification of cAMP levels in the DG of naive Ts65Dn and 2N mice. (FIG. 2A) Location of a micro-punch through the DG of the hippocampus that was analyzed here. (FIG. 2B) We found a significant reduction in cAMP levels in DG area of Ts65Dn mice compared with 2N mice. (2N=10.540±0.34 pM/ml, n=3, Ts65Dn=8.182±0.31 pM/ml, n=5, t=4.820, **P=0.002).

FIGS. 3A-3H: Immunocytochemical visualization of synaptosphysin (FIG. 3A) and β2AR (FIG. 3B) in DGCs. (FIG. 3C) We found that the majority of synaptophysin-stained puncta in DGC's soma and cell membrane also contained β2AR immunostaining. Images taken from DGC cell bodies (FIG. 3D) were processed for deconvolution (FIG. 3E) and a mask (FIG. 3F) automatically generated by IMAGE-PRO® Plus was superimposed on each image. (FIG. 3G) This was followed by quantification of the area occupied by the mask. (FIG. 3H) Quantification of the immunoreactivity for β2ARs showed a significant shift to higher values in adult Ts65Dn mice compared with 2N controls ($X^2=91.343$, $p<0.0001$), (2N-nadolol: n=9, 2N-formoterol: n=7, Ts65Dn-nadolol: n=6, Ts65Dn-formoterol: n=6) Scale bar=10 μm (FIGS. 3A-3C) and 20 μm (FIGS. 3D-3G). β2IR, β2 Immuno-reactivity.

FIGS. 4A-4B: Effects of formoterol treatment on vital signs of Ts65Dn and 2N mice. (FIG. 4A) No significant effects of formoterol were found on the heart rate ($P=0.369$, $F=0.839$). Similarly, ANOVA showed no significant effects of genotype ($P=0.104$, $F=2.852$) on the heart rate in treated mice (heart rate measured in pulse per minute: 2N-nadolol=660.981±35.86, n=9, 2N-formoterol=638.440±44.77, n=7, Ts65Dn-nadolol=677.740±40.11, n=6, and Ts65Dn-formoterol=672.620±36.58, n=6). (FIG. 4B) No significant effects of formoterol were found on the respiratory rate ($P=0.770$, $F=0.09$). However, we found significant effects of genotype on respiratory rate in treated mice ($P=0.002$, $F=11.82$) (respiratory rate per minute: 2N-nadolol=165.560±5.22, n=9, 2N-formoterol=165.890±5.99, n=7, Ts65Dn-nadolol=185.700±5.34, n=6, and Ts65Dn-formoterol=189.090±8.40, n=6). Fisher's post-hoc analysis also showed significantly higher respiratory rate in Ts65Dn mice and their 2N counterparts (*$P=0.028$). Similarly, Ts65Dn mice treated with formoterol also showed significantly higher respiratory rate compared to their 2N mice (**$P=0.018$).

FIGS. 5A-5D: The effects of formoterol treatment on mean velocity in Ts65Dn and 2N mice. (FIG. 5A) ANOVA showed significant effects of both genotype (*$p<0.001$, $F=12.72$) and treatment ($P=0.005$, $F=8.97$) on velocity. Fisher's post-hoc analysis showed formoterol treatment led to a significant reduction in velocity in Ts65Dn mice ($P=0.0014$) and a modest but not significant decrease in velocity in 2N mice ($P=0.468$) (velocity in mm/s: 2N-nadolol=31.465±2.74, n=15, 2N-formoterol=27.523±1.72, n=7, Ts65Dn-nadolol=52.965±4.59, n=12, Ts65Dn-Formoterol=33.682±3.85, n=7). (FIG. 5B) A similar effect was found in the total distance travelled in 10 minutes (ANOVA, genotype: *$p<0.001$, $F=12.35$, and treatment: $P=0.004$, $F=9.38$). Fisher's post-hoc analysis showed formoterol treatment led to a significant reduction in the distance travelled in Ts65Dn mice ($P=0.001$) and a modest decrease in 2N mice ($P=0.465$) (total distance travelled in meters: 2N-nadolol=18.233±1.48, n=15, 2N-formoterol=15.989±0.96, n=7, Ts65Dn-nadolol=30.424±2.70, n=12, Ts65Dn-formoterol=19.224±2.02, n=7). (FIGS. 5C, 5D) Quantification of the velocity of each mouse within the first 10 minutes of exposure to the open field arena. Formoterol treatment caused significant reduction in the velocity of Ts65Dn mice throughout the 10 minute exposure to the open field arena.

FIGS. 6A-6C: (FIG. 6A) Formoterol treatment restored synaptic density in the DG in Ts65Dn mice. Quantifying the percentage of area covered by synaptophysin staining showed a significant effect of genotype on synaptophysin (**$P=0.008$, $F=8.455$). Fisher's post hoc analysis showed a significant decrease in the synaptic load in adult Ts65Dn mice compared with their corresponding 2N group (2N-nadolol=27.40±11.00%, n=6, and Ts65Dn-nadolol=21.50±1.00%, n=7, $P=0.008$). Treatment with formoterol led to a significant increase in synaptophysin load in Ts65Dn mice (Ts65Dn-nadolol=21.50±1.00% and Ts65Dn-formoterol=25.80±2.00%, n=7 *$P=0.035$). No significant effects of formoterol were found in the 2N group (2N-nadolol=27.40±11.00% and 2N-formoterol=28.50±2.00%, $P=0.627$). (FIG. 6B) We found a significant reduction in the density of c-Fos-positive DGCs in Ts65Dn mice compared with 2N mice (2N-nadolol=179.30±22.4 cells/mm², n=6 and Ts65Dn-nadolol=109.42±13.0 cells/mm², n=7, $P=0.0072$). Interestingly, treating Ts65Dn mice with formoterol led to a significant increase in the density of c-F0s-positive DGCs in these mice compared to 2N controls (Ts65Dn-formoterol=189.60±14.60 cells/mm², n=6 2N-formoterol=151.25±15.20 cells/mm², n=6,*$P=0.00014$). Two-way ANOVA showed a significant interaction between genotype and treatment ($F=10.706$, $P=0.00335$) on the density of c-Fos-positive DGCs. (FIG. 6C) Quantifying the density of c-Fos-positive cells in the DGC region across the rostro-caudal axis of the hippocampus in Ts65Dn mice showed that formoterol led to a significant increase in the density of c-Fos positive cells throughout along the rostro-caudal axis the hippocampus in these mice (***$P<0.001$, and *$P<0.05$, the x-axis shows section number along the rostro-caudal axis of hippocampus).

FIGS. 7A-7D: (FIG. 7A) Immunocytochemical visualization of GFAP in the DG of a 2N mouse (Scale bar: 20μ GFAP-positive profiles were mainly detected among the DGC somata and in both polymorphic and the ML of the DG. DGC, dentate granule cell; ML, molecular layer; PML, Polymorphic Layer. (FIGS. 7B-7D) Frequency distribution of distances of GFAP-positive profiles from the DGC area. Although we found no differences in the frequency distribution of the distance from the DGC layer between the 2N and Ts65Dn mice treated with nadolol ($X^2=3.46$, $P=0.983$), a significant increase in distance of astrocytes was observed in Ts65Dn treated with formoterol ($X^2=21.103$, $P=0.032$). No significant effects of formoterol were found in the 2N group ($X^2=16.90$, $P=0.110$).

FIGS. 8A-8H: (FIGS. 8A-8C) BrdU-positive profiles (arrows) in the DG of a 2N mouse [Scale bar=300μ (FIG. 8A), 100μ (FIG. 8B), 80μ (FIG. 8C)]. (FIG. 8D) The total number of BrdU-positive profiles in the DG was 37% lower numbers in Ts65Dn mice compared to 2N controls. Formoterol increased the number of BrdU-positive cells in DG in Ts65Dn mice and their 2N controls. ANOVA showed significant effects of treatment ($P=0.018$, $F=6.749$) and no effects of genotype ($P=0.762$, $F=0.094$) on number of BrdU-positive profiles. Post-hoc test showed that formoterol treatment caused a significant increase in the number of BrdU-positive profiles in Ts65Dn mice (*$P=0.031$). (2N-nadolol=3,161.930±900, n=5, 2N-formoterol=5, 145.970±1051, n=6, Ts65Dn-nadolol=2,133.290±491, n=5, and Ts65Dn-formoterol=5,539.600±1301). (FIG. 8E) DCX-positive neurons in the DG of a 2N mouse; Scale bar=170 μm. (FIG. 8F) The number of DCX-positive DGCs in 2N and Ts65Dn mice. ANOVA showed significant effects of genotype ($P=0.0001$, $F=21.50$) and no effects of treatment on the number of DCX-positive cells. Post-hoc analysis showed a significant ($P=0.004$, 2N-nadolol=5391.36±744, n=6; Ts65Dn-nadolol=2837.79±500, n=6) decrease in the number of DCX-positive neurons in Ts65Dn mice compared with 2N mice. No significant effects of formoterol were found in either genotype (2N-formoterol=5148.91±350, Ts65Dn-formoterol=2619.28±508). (FIG. 8G) The order of branching in Ts65Dn and 2N mice. (2N-nadolol=2.05±0.12, n=6, 2N-formoterol=1.66±0.08, n=6, Ts65Dn-nadolol=1.58±0.08, n=7, Ts65Dn-formoterol=2.24±0.10, n=8). A significant interaction of genotype and treatment ($P=0.0001$, $F=26.06$) was found on the order. Post-hoc showed a significant reduction in the order in Ts65Dn compared with 2N ($P=0.004$). Furthermore, a significant positive effect of formoterol was found in Ts65Dn mice (***$P=0.000075$). Interestingly, a significant reduction was found in 2N-formoterol compared with 2N-nadolol (*P=0.018). (FIG. 8H) The increase in the dendritic span in the formoterol-treated Ts65Dn mice has been clearly demonstrated.

FIG. 9 shows the effects of intranasal delivery of formoterol on spatial learning in Ts65Dn mice and their 2N controls. A significant increase in the number of errors and the time to reach the hidden platform was observed in saline-treated Ts65Dn mice as compared to their 2N counterparts. However, no significant differences were observed between formoterol-treated Ts65Dn mice and their 2N controls. Thus, intranasally delivered β1- and/or β2-ADR agonists are effective in improving spatial learning in Ts65Dn mice, which are an art-accepted animal model for human DS.

FIG. 10 shows average values of the total time and the number of errors made by Ts65Dn mice and 2N controls treated with intranasal formoterol. Significant effects of formoterol were observed in reducing both time and number of errors in Ts65Dn indicating that formoterol led to a significant improvement in spatial learning in Ts65Dn mice. This suggests a similar improvement is provided for DS humans.

In the above examples, formoterol is a representative example of both β2-ADR selective or partial agonists in the context of the present invention which specifically uses intranasal administration.

By administering the one or more β2-ADR agonists or compositions containing the same intranasally, it is not necessary to co-administer β1-ADR antagonists, such as nadolol, in order to minimize or eliminate peripheral effects. Hence, intranasal administration of these compounds and/or compositions containing the same afford an important advantage over administration by intravenous or intraperitoneal injection. As noted above, intranasal administration of these compounds and compositions avoids peripheral effects which are adverse to the cardiovascular health of DS humans. β1-ADR antagonists or blockers may be used if desired, however, but they are not necessary to practice the present invention.

The β2 agonists and β1 antagonists or blockers may be administered intranasally by either spray or dry powder. Generally, individual human doses of the one or more β2-ADR agonists range from about 2 to 100 mg per administration. It is preferable, however, that the individual dose be from about 5 to 30 mg per administration. The one or more β2-ADR agonists may be intranasally administered in sterile saline or dextrose saline solution, for example 0.9% by weight sterile aqueous saline solution. A typical concentration of the one or more β2-ADR agonists in aqueous based solvent is about 2-20 μg/l, and more particularly 5 μg/l to 15 μg/l.

Generally, the compounds or compositions of the present invention are administered by a nebulizer nose inhaler or a dry powder nose inhaler. See U.S. Pat. No. 7,569,586, which is incorporated herein in the entirety. The compounds or compositions of the present invention may be formulated and administered as described in U.S. Pat. No. 7,569,586, however, without using the additive drugs, such as muscarinic antagonists, antihistamines and steroidal anti-inflammatory compounds, which would otherwise be used in treating pulmonary disorders, such as COPD (chronic obstructive pulmonary disorder) or asthma. However, medically inactive additives and diluents many be used as described in U.S. Pat. No. 7,569,586.

Additionally, nose drop and/or nose liquid spray formulations are also advantageous. For example, the one or more β2-ADR compounds may be formulated in a nasal spray as described in U.S. Pat. No. 5,760,237, which is incorporated herein in the entirety.

Single or multiple administrations may be used for the one or more β2-ADR agonists or any compositions containing them. For example, during a course of treatment, a steady state level of β2-ADR agonist in a patient over a period of time may be accomplished by use of multiple treatments in series as indicated by a treating physician, and based upon test results before and after treatment.

Additionally, however, the present invention specifically contemplates the treatment of children having DS. Specifically, treatment of children at age 5 or older is advantageous in order to increase dendritic complexity of cells in dentate gyms, for example, as early in human brain development as possible. The dosage levels described above may be used for both children and adults in both single and multiple treatments.

Specific exemplary combinations of the one or more β2-ADR agonists are salbutamol and salmeterol, or terbuline and bambuterol, or procaterol and formoterol or salts thereof. However, as already noted, any single β2 agonist, such as formoterol or salt thereof may be used in either single or multiple treatments in series. As noted, any combination of β2-ADR agonists may be used. For example, combinations may include formoterol or salts thereof, salbutamol or salts thereof, or salmeterol or salts thereof. Exemplary salts are, for example, formoterol fumarate dehydrate. In addition to salts, hydrates of salts are specifically contemplated.

Additionally, buffers and additives may be mixed with the nasal formulations of the present invention. For example, sodium chloride may be added as would be the case if dextrose-5%-saline or a saline solution is used as a solvent. Also, buffers such as citric acid and sodium citrate may be used to adjust the pH of the solution to about 5.0.

EXAMPLES

Methods
1) Acclimation and Drug Delivery

Mice were acclimated to handling for a period of two weeks before the onset of intranasal dosing. Acclimation helped to ensure a correct body position for maximum effectiveness of awake intranasal drug delivery. In addition, acclimation prevented the occurrence of anxiety reaction after dosing. Mice spent about 2-3 days on each of nine steps before progressing to the next step, depending upon the animal's comfort to handling. The mouse's stress level was used as a measure of progress. To do this, the mouse's movements, the amount and frequency of urination, defecation, trembling and biting were assessed. In case that a mouse showed high levels of stress response, the process was elongated for the mouse at this step:

a) Days 1 and 2:

The mouse was placed on the palm of the hand for a period of two to three minutes, no more than one foot above the cage top, as animals frequently jump during this introductory step.

b) Days 3 and 4:

The mouse was placed in the palm of the hand for three minutes and was gently petted. Petting was done unidirectionally from the head to the tail, while allowing the mouse to move about freely.

c) Days 5 and 6:

The mouse was placed in the palm of the hand for three minutes while massaging behind the ears (lightly pinching together the skin on the back of the neck using the thumb and the pointer finger).

d) Days 7 and 8:

The mouse was held by the scruff for 30 sec., letting the mouse rest on the cage top for another 30 sec.

e) Days 9 and 10:

The mouse was held using the intranasal grip, without inverting the animal for 30 sec.

f) Days 11 and 12:

The mouse was held with the intranasal grip including inverting the animal so its ventral side is facing up towards the ceiling for 30 sec. This was repeated after a one-minute rest period.

g) Days 13 and 14:

The mouse was held with the intranasal grip, then inverted, and then a pipettor was briefly placed over each nostril for 30 sec. This was repeated after a one-minute rest period.

h) Days 15 and 16:

1) The mouse was held with the intranasal grip, then inverted, and 6 µl of saline solution was intranasally administered into both left and right nares.

2) The mouse was held with the intranasal grip, then inverted, and 6 µl of saline solution was intranasally administered into the left and right nare twice placing the animal back on the cage top in between.

i) Intranasal Dosing:

Mice were treated with either saline solution or formoterol solution for 5 days.

Formoterol was administered at 2 mg per kg of body weight from a stock solution of formoterol dissolved in dimethyl sulfoxide (DMSO) at a concentration of 5 mg/ml.

1) The mouse was removed from the cage and kept on cage top during the dosing.

2) The intranasal grip was used to pick up the mouse.

3) Using the dominant hand, the pipettor was loaded with up to 6 µl of drug or vehicle. The tip of filled pipettor was placed near the mouse's left nostril at a 45 degree angle and the drug was administered slowly with about half of the volume (i.e., 3 µl).

4) The droplet was placed close enough to the mouse's nostril so that the mouse can inhale the droplet. Immediately after the mouse inhales this small drop, the rest of the drug was collected with the pipette tip to form another small droplet for the mouse to inhale through the same nostril about 2-3 sec. later.

5) The mouse was held in this position for 15 sec.

6) Steps 3-5 were repeated for the right nostril.

7) The mouse was placed back on top of his cage for 2 min. and the entire process was repeated starting 2 min. after delivery of the first drop. All together the mouse received four drops of up to 6 µl each totaling a maximum volume of 24 µl of solution.

3) Radial Arm Water Maze:

The training began on the $4^{th}$ day of intranasal dosing.

The testing day was done on the $5^{th}$ and final day of dosing.

The first trial for each mouse was done 3 hours post-intranasal dose.

Preparation

A day before testing, the pool was inspected for any damage or leaks.

The pool was filled with water until it was high enough just to cover the hidden platform by about 0.5 cm., but low enough that the visible platform was not covered.

White tempera paint was added to the water to obscure visibility of the platform.

The pool dividers were placed.

A pool thermometer was placed not visible to the mice (behind the inserts).

The visible and hidden platforms were placed so they may equilibrate to pool temperature.

Day 1: Training

Trial 1: Visible Platform

1) Each mouse was placed into a cage with no bedding lined with a dark terry cloth washcloth.

2) The cages were placed under a heat source while testing.

3) Placed visible platform in goal location for mouse being tested as specified on the score sheet.

4) Beginning with the visible escape platform in the assigned arm, mouse 1 of cohort 1 is placed gently into the pool near the perimeter of the wall of the first start arm (specified on the score sheet) and facing the center of the pool.

5) The trial lasted up to 60 sec.

6) The number of incorrect arm entries was quantified. Entries into the goal arm were not counted as errors, even if the platform was not located. An entry was considered to occur when all four legs of the mouse had entered the alley completely and the mouse was parallel to the alley walls. Failure to select an arm after 15 sec. from start time was considered as an error.

7) After 1 min., if the platform had not been located, the mouse was guided gently through the water through the platform.

8) The mouse was placed on the platform.

9) Whether the mouse was guided or the mouse located the platform within the 1 min., the mouse was allowed to stay on the platform for 15 sec. Record the number of errors and time to complete the trial on the score sheet.

10) The mouse was removed and gently dried using a dry towel before returning to its cage under a heat lamp.

11) The visible platform was relocated to a new location for the next mouse.

Trial 2: Hidden Platform

After all four mice in the first cohort have had a trial, platforms are switched from visible to hidden.

12) Hidden platform is placed in goal arm location appropriate for the mouse being tested.

13) Beginning with mouse 1 cohort 1, steps 5-14 are repeated.

14) Steps 5-14 are repeated for mice 2 and 3 from cohort 1.

Trial 3: Visible Platform

After all mice in the first group have had a trial the platforms were switched from hidden to visible.

15) Beginning with mouse 1 of cohort 1, the visible platform was placed again in its assigned arm and the test was performed as in steps 5-14.

Trial 4: Hidden platform

After all four mice in the first cohort completed trial 3, platforms were switched from visible to hidden.

Trial 5: Visible platform

After completing trial 4, platforms were switched from hidden to visible.

Trial 6: Hidden platform

After all mice in the first cohort completed trial 5, platforms were switched from visible to hidden.

16) Beginning with mouse 1 of cohort 1, the hidden platform was placed again in its assigned arm and performed the test as in steps 5-14.

17) Keeping the mice from cohort 1 warm, steps 5-22 were repeated with the mice from the second cohort for trials 1-6. This assured that the mice from cohort 1 rested while mice from cohort 2 were tested.

18) Steps 5-22 were repeated with the mice from the first cohort for trials 7-12.

19) Steps 5-22 were repeated with the mice from the cohort 2 for trials 7-12.

20) Steps 5-22 were repeated with the mice from cohort 2 for trials 7-12.

21) Steps 5-22 were repeated again for cohort 2 ensuring that all trials were performed using the hidden platform.

22) The mice were allowed to dry and warm up before returning to their home cages.

Day 2: Testing

First trial of testing day occurred 24 hours from first trial of training day.

Steps 5-32 were repeated using the same mice in exactly the same groups except this time using only the hidden platform for all 15 trials again.

Additional Examples

An eight (8) year old child having DS, and having a body weight of 35 kg is treated multiple times with formoterol in saline solution in order to increase cognitive function, and to preclude or minimize adult onset of AD brain pathology.

Over a period of 6 weeks, the child is treated as follows:

Child is subjected to contextual learning testing, 2 hours later, 6 mg of formoterol is administered intranasally by drops (formoterol in 0.9% by wt. saline) once or twice weekly for 3 weeks, Child is again subjected to contextual learning testing after the cessation of the treatment regime to determine the adequacy of treatment or whether further treatment is necessary. Improvements in any one or more test scores are indicative of treatment success.

Over a period of 10 years, the same child may, in the alternative, be treated as follows:

Child is subjected to contextual learning testing, 2 hours later, 7 mg of formoterol is administered intranasally by nasal spray (formoterol in 0.9% saline) once per month over a period of 2 years, Child is again subjected to contextual learning testing at the end of each year during the duration of period to determine the adequacy of treatment or whether further treatment is necessary. Improvements in any test scores are indicative of treatment success.

Contextual learning is a major part of learning and memory that fails in humans with DS. Contextual learning is also a reliable means of conducting memory assessment in mice. In fact, learning and memory in both humans and mice appears to be related to attention. For example, in studies with mice, mice that failed to pay attention to context, also failed to remember it.

Contextual learning is mediated by the hippocampus, and any problems with hippocampal structure, particularly the dentate gyms, would lead to abnormalities in contextual learning.

Intranasal administration of the one or more β2 agonists to humans with DS, both adult and child, in accordance with the present invention has the advantage of reducing the severity of hyperactivity. Hyperactivity, in turn, may well be a sign of attention deficit, and addressing this additional problem helps to improve cognitive function. Further, with intranasal administration, it is unnecessary to co-administer any β1-adrenergic receptor antagonists in order to inhibit peripheral effects.

Any accepted contextual learning tests used in the present invention to both assess baseline cognitive function and to measure or quantify improved cognitive function may be used. For example, the contextual learning test used may be based upon single task learning, multiple task learning or spatial contextual memory. Contextual learning test evaluations based upon spatial contextual memory are advantageous in assessing, for example, how well an individual is able to navigate a shopping mall, his or her neighborhood or a city transit or subway system as well as assessing any improvements in the ability to execute these tasks resulting from the treatment methods described herein.

An example of a simple spatial contextual learning test is contextual cuing, where humans learn to use repeated spatial configurations to facilitate a target search. A higher order spatial contextual learning test is serial learning, where humans learn to use subtle sequence regularities to respond more quickly and accurately to a series of events. See, for example, J. H. Howard Jr., et al, Neuropsychology, Vol. 18(1), January 2004, 124-134.

A particularly advantageous testing protocol that may be used is the Arizona Cognitive Test Battery (ACTB). See Edgin, J., et al. J. Neurodevelop. Disord. (2010) 2: 149-164. The ACTB has been developed specifically to assess the cognitive phenotype in DS, and includes various tests with various task demands and links with brain function. In more detail, tests are included for: 1) benchmarks, such as KBIT II verbal subscale and KBIT II non-verbal subscale IQ tests, 2) hippocampal function, 3) prefrontal function, 4) cerebellar function, 5) Finger sequencing tasks, 6) NEPSY visuo-motor precision and 7) simple reaction time.

A correlation of domain/test, test description and primary ability assessed in accordance with the ACTB is provided below:

| Domain/Test | Description | Primary Ability Assessed |
|---|---|---|
| 1) Benchmark KBIT-II verbal subscale | Points to pictures based on word or phrase | Verbal comprehension |
| KBIT-II nonverbal subscale | Semantic or visuo-spatial pattern completion | Problem solving |
| 2) CANTAB spatial span | Touching boxes in order of Changing color on screen | Immediate memory for spatial-temporal sequence |
| 3) Prefrontal Modified dots task | Press button below a cat, shifts to new rule, press across screen for a frog, etc. | Inhibitory control working memory |
| 4) CANTAB IED | Forced-choice discrimination task with change in relevant dimension | Set-shifting |

-continued

| Domain/Test | Description | Primary Ability Assessed |
|---|---|---|
| 5) Hippocampal CANTAB paired associates | Recall for hidden abstract patterns | Spatial associative memory |
| 6) Virtual computer-generated arena | Navigation of a virtual arena(via joystick) to find a hidden target | Spatial memory |
| 7) Cerebellar Finger-sequencing task | Sequences generated by tapping a number of fingers (1, 2, 3, 4) to a lever in succession | Motor sequencing |
| 8) NEPSY visuomotor precision | Follows two tracks with a pen | Visuo-motor tracking, hand-eye coord. |
| 9) CANTAB simple reaction time | Participants press button in response to a box presented on a screen | Motor response time and attention |

The above battery of tests are generally all performed in order to assess all major cognitive processes known to be affected by DS balanced by the practical need for testing under time constraints. The ACTB affords an advantageous manner of evaluating the effects of the present invention on individuals with DS.

Generally, the battery of tests are conducted with a test group of about 80 DS individuals, and a control group of about 80 DS individuals. The test group is treated with any of the treatment regimes described herein, and the control group is treated with placebo, such as a dextrose 5% saline solution by intranasal administration.

Additionally, the treatment regimes described above may be given individually, but the effects of the treatment regimes are analyzed using test groups of about 80 versus control groups of about 80 as described above.

An improvement in cognitive function as defined herein as being at least a 10%, and preferably at least a 20% score improvement, on at least one, and preferably two or more, of the tests listed in the ATCB, for example. Anyone of the domain/tests listed for the ATCB above may be included in assessing whether an improvement occurred. Testing may be conducted after treatment or during treatment to ascertain whether modifications in dosage or frequency of treatment is warranted.

Furthermore, the present invention also provides a method of inhibiting onset of adult AD brain pathology in a child having DS, which entails intranasally administering one or more β2 adrenergic receptor agonists to the child in an amount and with a frequency of administration effective to inhibit the onset.

Generally, any non-invasive procedure many be used to both establish a baseline of brain pathology (existent or non-existent) from which baseline a treatment protocol is established. However, magnetic resonance imaging (MRI) is preferred for neuroimaging examination because it allows for accurate measurement of the 3-dimensional (3D) volume of brain structures, especially the hippocampus and related regions. Such techniques are well known as described in U.S. Pat. No. 6,490,472, which patent is incorporated herein in the entirety. Other techniques, such as fluorodeoxyglucose positron emission tomography (FDG-PET) may also be used for neuroimaging.

Moreover, non-invasive optical imaging systems may also be used for monitoring early AD pathological events. See, for example, U.S. patent publication 2011/0286932, which is incorporated herein in the entirety. The technique described therein entails administration of a fluorescent marker to a human (and for the present invention a DS human) for staining Aβ peptides, imaging the retina of the DS human with an optical imaging system, and examining the images for stained Aβ peptides in order to determine whether onset of AD brain pathology has occurred.

Additionally, test groups of about 80 individuals are used versus control groups of about 80 individuals. This treatment many also be used for treatment of single individuals in order to inhibit onset of adult AD brain pathologies in a child, or even in older individuals having AD.

Generally, intranasal administration to either an adult or child is conducted such that a standard dose of the one or more β2-ADR agonists is from about o.1 to 10 mg/kg of body weight. The term about means up to 0.05 mg/kg of body weight. Hence, the range of about 0.1 to 10 mg/kg of body weight is from 0.05 to 10.05 mg/kg of body weight. Preferably, the standard dose is from about 0.05 to 3 mg/kg of body weight. As noted above, this standard dose may be administered multiple times with varying time spaces in between serial doses. For example, the time spaces in between doses may be days, weeks or even months depending upon test results after one or more treatments and the judgment of a treating physician.

EXAMPLES

The following is a non-limiting example of preparation of a aqueous solution of the β2-ADR agonist, formoterol.

Formoterol is soluble in water to the extent of about 50 mmol/liter. Since, 1 mol of formoterol is 344 g.:

50 mmol/L×(1 mol/1000 mmol)×(344 g/mol)=17.2 g/L is an approximate upper limit of solubility for formoterol in water. But, this corresponds to 17,200 mg/L or 1.72 mg/ml, which means that at this solution concentration, a dose of 10 mg of formoterol may be administered in about 6 ml of solution. This concentration corresponds to a 1.72% solution. A 1% solution of formoterol in water may be prepared by dissolving 1 g of formoterol in 100 ml of water, or by dissolving 10 g of formoterol in 1000 ml (or 1 L) of water since 1 ml of water weighs about 1 g.

Solutions of any of all combinations of one or more β2-ADR agonists in water or other aqueous-based solvents, such as saline solution or dextrose-5%-saline, may be prepared in a similar manner.

The following are non-limiting examples of nasal formulations of the present invention.

Formoterol fumarate dihydrate is dissolved in a volume of aqueous solvent, such as saline solution sufficient to reach a concentration of about 1% by weight of formoterol based on the total weight of the solution. The solution may be warmed to about 40° C. to facilitate dissolution of the formoterol fumarate dehydrate. This solution may be used as is, or may be parceled out into small containers for retail sale with nose droppers by itself or in a kit.

Generally, the solutions of the present invention may be mixed as a stock solution from which diluter solutions may be prepared prior to administration of the diluter solution. Solutions for direct use are usually not above 2% by weight of β2-ADR agonist (based on the active portions of agonist) based on the total weight of the solution. Stock solutions may, for example, be 'n' times stronger than the diluter solution for use, but must then be diluted by a factor of l/'n' prior to use as the diluter solution.

The solution may, for example, be offered for use in a containing means accompanied by a nasal dropper having a calibrated drop tube. The calibrations are usually in ml of volume.

The containing means may be any type of container that is able to contain an aqueous solution, such as glass or plastic bottles, tubes, or even transparent straws. There is no limit to the containing means as long as it is able to contain the solutions of the present invention. The containing means may be assembled in the form of a kit which contains one or more applicators, such as nasal droppers or nasal swabs. The application of the aqueous solution of the present invention may be administered directly by a treating physician, or by the DS human on his/her own under the general care of a physician. Testing may be conducted periodically to monitor progress and to determine if dosages need be attenuated.

The present invention may be practiced with modifications within the skill of the artisan without departing from the spirit and scope thereof.

What is claimed is:

1. A method of improving cognitive functioning in a human having Down syndrome, which comprises the step of intranasally administering an amount of one or more β2-ADR agonists or pharmaceutically-acceptable salt or salts thereof to a human in an amount and with a frequency of administration effective to improve the cognitive functioning of said human, wherein said one or more β2-ADR agonists or pharmaceutically-acceptable salt or salts thereof are administered without co-administration of one or more β1-ADR antagonists.

2. The method of claim 1, wherein said one or more β2-ADR agonist is formoterol or a pharmaceutically-acceptable salt thereof.

3. The method of claim 1, wherein said one or more β2-ADR agonists are administered intranasally by drops from a dropper.

4. The method of claim 1, wherein said one or more β2-ADR agonists are administered intranasally by dry powder inhalation.

5. The method of claim 1, wherein said one or more β2-ADR agonists are administered intranasally by nasal spray.

6. The method of claim 2, wherein a salt of formoterol is used, which is formoterol fumarate dihydrate.

7. The method of claim 1, wherein the human is a child.

8. The method of claim 1, wherein the human is an adult.

9. The method of claim 1, which further comprises measuring the improved cognition by a contextual learning test after one or more intranasal administrations.

10. The method of claim 9, wherein the improved cognition is measured by ATCB testing.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
aaatcgtgcg tgacatcaaa                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2
aaggaaggct ggaaaagagc                                               20

<210> SEQ ID NO 3
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 3
tgcaccaact gcttagc                                                  17

<210> SEQ ID NO 4
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 4
ggcatggact gtggtcatga g                                             21

<210> SEQ ID NO 5
<211> LENGTH: 19
<212> TYPE: DNA
<213> ORGANISM: Artificial Sequence
<220> FEATURE:
<223> OTHER INFORMATION: Synthetic polynucleotide
```

```
<400> SEQUENCE: 5
caccaggcca cttcaagga                                                    19

<210> SEQ ID NO 6
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 6
gatggatgcg caggaagaa                                                    19
```